United States Patent
Wang et al.

(10) Patent No.: US 9,458,162 B2
(45) Date of Patent: Oct. 4, 2016

(54) CYCLIC MOLECULES AS BRUTON'S TYROSINE KINASE INHIBITORS

(71) Applicant: Nanjing Allgen Pharma Co. Ltd., Nanjing (CN)

(72) Inventors: Zhaoyin Wang, Kirkland (CA); Lianhai Li, Pierrefonds (CA); Zhigang Wang, Lachine (CA)

(73) Assignee: Nanjing Allgen Pharma Co. Ltd., Nanjing (CN)

( * ) Notice: Subject to any disclaimer, the term of this patent is extended or adjusted under 35 U.S.C. 154(b) by 0 days.

(21) Appl. No.: 14/375,539

(22) PCT Filed: Jan. 30, 2013

(86) PCT No.: PCT/CA2013/000085
§ 371 (c)(1),
(2) Date: Jul. 30, 2014

(87) PCT Pub. No.: WO2013/113097
PCT Pub. Date: Aug. 8, 2013

(65) Prior Publication Data
US 2015/0011530 A1    Jan. 8, 2015

Related U.S. Application Data

(60) Provisional application No. 61/632,781, filed on Jan. 31, 2012.

(51) Int. Cl.
| | | |
|---|---|---|
| C07D 487/04 | (2006.01) | |
| C07D 471/04 | (2006.01) | |
| A61K 31/519 | (2006.01) | |
| A61P 19/02 | (2006.01) | |
| A61K 31/438 | (2006.01) | |
| A61K 45/06 | (2006.01) | |
| C12N 9/99 | (2006.01) | |

(52) U.S. Cl.
CPC ........... *C07D 487/04* (2013.01); *A61K 31/438* (2013.01); *A61K 31/519* (2013.01); *A61K 45/06* (2013.01); *C07D 471/04* (2013.01); *C12N 9/99* (2013.01); *C12Y 207/10002* (2013.01)

(58) Field of Classification Search
CPC .......................... C07D 487/04; A61K 31/519
USPC .................... 544/262, 280; 514/262.1, 265.1
See application file for complete search history.

(56) References Cited

U.S. PATENT DOCUMENTS

| | | | | |
|---|---|---|---|---|
| 6,713,474 B2 * | 3/2004 | Hirst | ................... | C07D 487/04 514/218 |
| 6,921,763 B2 * | 7/2005 | Hirst | ................... | C07F 9/6561 514/262.1 |

FOREIGN PATENT DOCUMENTS

| | | |
|---|---|---|
| CA | 2 344 249 A1 | 3/2000 |
| CA | 2 730 606 A1 | 1/2010 |

OTHER PUBLICATIONS

Whang et al., Drug Discovery Today, pp. 1-5, 2014.*
Akinleye et al. Journal of Hematology & Oncology 2013, 6:59.*
Chakravarty et al. Clinical Immunology (2013) 148, 66-78.*
Cecil Textbook of Medicine, edited by Bennet, J.C., and Plum F., 20th edition,vol. 1, 1004-101 O, 1996.*
International Search Report corresponding to PCT/CA2013/000085 mailed Apr. 9, 2013 (4 pages).

* cited by examiner

*Primary Examiner* — Venkataraman Balasubramanian
(74) *Attorney, Agent, or Firm* — Kilpatrick Townsend & Stockton LLP

(57) ABSTRACT

The present document describes novel molecules having protein tyrosine kinase inhibitory activity, and methods of synthesizing and using such compounds. More specifically, the present document describes compound of Formula (A): (Formula (A)) or a pharmaceutically acceptable salt, hydrate or solvate thereof, and methods of synthesizing and using such compounds.

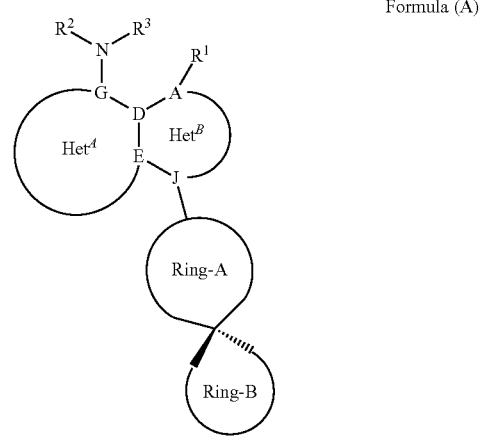

Formula (A)

6 Claims, No Drawings

CYCLIC MOLECULES AS BRUTON'S TYROSINE KINASE INHIBITORS

CROSS-REFERENCE TO RELATED APPLICATIONS

This application claims priority of U.S. provisional patent application 61/632,781, filed on Jan. 31, 2012, the specification of which is hereby incorporated by reference.

BACKGROUND (a) Field

The invention relates generally to novel chemical compounds and methods. More particularly, the invention provides novel molecules, having protein tyrosine kinase inhibitory activity, and methods of synthesizing and using such compounds. Preferred compounds are Bruton's tyrosine kinase (BTK) inhibitors useful for the treatment of allergic disorders, autoimmune disease, inflammatory disease, and cancers, as well as the treatment of B-cell lymphoma and leukemia.

(b) Prior Art

Protein kinases, the largest family of human enzymes, encompass well over 500 proteins. Bruton's Tyrosine Kinase (BTK) is a member of the Tec family of tyrosine kinases, and is a regulator of early B-cell development as well as mature B-cell activation, signalling, and survival. BTK has emerged as a new molecular target for the treatment of B cell lymphoma, leukemia and autoimmune disorders.

This invention concerns novel cyclic compounds that are BTK inhibitors and their use in treating cancers and other diseases mediated by BTK.

SUMMARY

According to an embodiment, there is provided a compound of Formula (A)

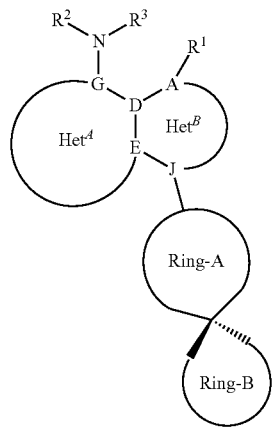

Formula (A)

or a pharmaceutically acceptable salt, hydrate or solvate thereof, wherein:

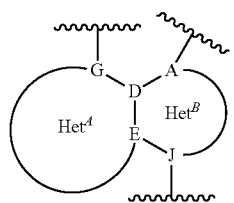

may be selected from:

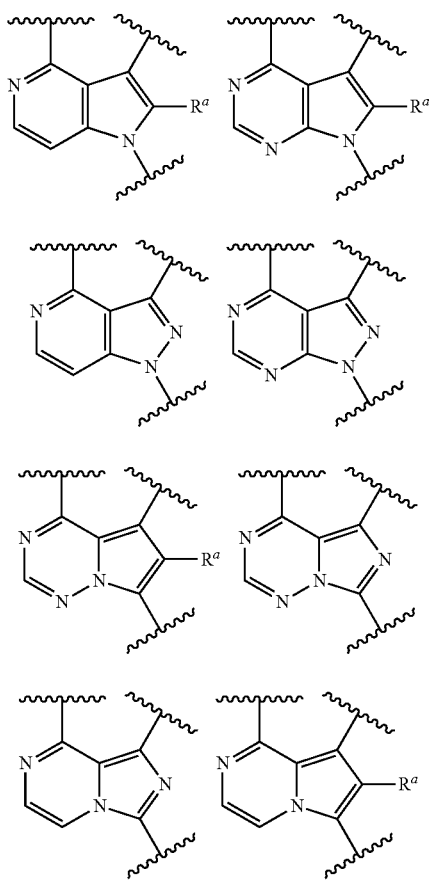

$R^a$ may be H, halogen, $L_1$-(substituted or unsubstituted $C_1$-$C_3$ alkyl), $L_1$-(substituted or unsubstituted $C_2$-$C_3$ alkenyl), $L_1$-(substituted or unsubstituted heteroaryl), or $L_1$-(substituted or unsubstituted aryl), wherein $L_1$ may be a bond, O, S, —S(=O), S(=O)$_2$, S(=O)$_2$—NH, NH, C(O), —NHC(O)O, —OC(O)NH, —NHC(O), or —C(O)NH;

$R^1$ may be H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), $L_2$-(substituted or unsubstituted aryl)-$L_2$-(substituted or unsubstituted aryl), $L_2$-(substituted or unsubstituted aryl)-$L_2$-(substituted or unsubstituted heteroaryl), $L_2$-(substituted or unsubstituted heteroaryl)-$L_2$-(substituted or unsubstituted aryl), $L_2$-(substituted or unsubstituted heteroaryl)-L₂-(substituted or unsubstituted heteroaryl), wherein L$_2$ may be a bond, O, S, —S(=O), —S(=O)$_2$, C(=O), -(substituted or unsubstituted C$_1$-C$_5$alkyl), or -(substituted or unsubstituted C$_2$-C$_6$alkenyl);

R$^2$ and R$^3$ may be independently selected from H, C$_1$-C$_8$alkyl and substituted C$_1$-C$_8$ alkyl;

Ring A may be a 3 to 12 membered carbocyclic ring; or

Ring A may be a 3 to 12 membered carbocyclic ring in which one or more carbon ring atoms may be replaced with one or more O, S, —C(O)—, —C(S)—, NR$^c$, or Ring A may be a 3 to 12 membered carbocyclic ring which unsubstituted or substituted with one or more R$^c$; or Ring A may be a 3 to 12 membered carbocyclic ring in which one carbon ring atoms may be replaced with a nitrogen atom and the nitrogen atom in Ring A may be connected with J when J may be a carbon atom;

R$^c$ may be independently chosen from halogen, C$_{1-12}$alkyl, C$_{2-12}$ alkenyl, C$_{2-12}$ alkynyl, C$_{3-12}$ cycloalkyl, C$_{6-12}$ aryl, a 3-12 membered heteroalicyclic ring, a 5-12 membered heteroaryl ring, —NH$_2$, —CN, —OH, —O—(CH$_2$)$_n$C$_{3-12}$cycloalkyl, —O—(CH$_2$)$_n$C$_{6-12}$aryl, —O—(CH$_2$)$_n$(3-12 membered heteroalicyclic ring) or —O—(CH$_2$)$_n$(5-12 membered heteroaryl ring), with the proviso that when R$^c$ is halogen, —CN, —OH, —O—C$_{1-12}$alkyl, —O—(CH$_2$)$_n$C$_{3-12}$cycloalkyl, —O—(CH$_2$)$_r$, C$_{6-12}$aryl, —O—(CH$_2$)$_n$(3-12 membered heteroalicyclic ring) or —O—(CH$_2$)$_n$(5-12 membered heteroaryl ring), R$^c$ may be connected to an atom different than nitrogen, Ring B may be a 3 to 12 membered carbocyclic ring; or Ring B may be a 3 to 12 membered carbocyclic ring in which one or more carbon ring atoms may be replaced with one or more O, S, S(O), S(O)$_2$, C(O), C(S), N—X; or Ring B may be a 3 to 12 membered carbocyclic ring which may be unsubstituted or substituted by X, —NR$^d$—X or C$_1$-C$_6$alkyl-NR$^d$X;

R$^d$ may be H, C$_{1-6}$alkyl, C$_{3-6}$cycloalkyl, aryl or heteroaryl;

X may be:

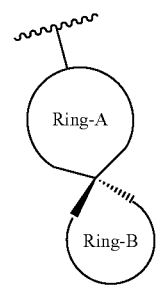

wherein

R$^5$, R$^4$ and R$^6$ may be independently selected from H, C$_{1-12}$ alkyl, C$_{1-12}$heteroalkyl, C$_{1-12}$ heterocycloalkyl, C$_{2-12}$ alkenyl, C$_{2-12}$ alkynyl, C$_{3-12}$ cycloalkyl; and n may be selected from 1 to 6.

According to another embodiment, there is provided a compound of Formula (B)

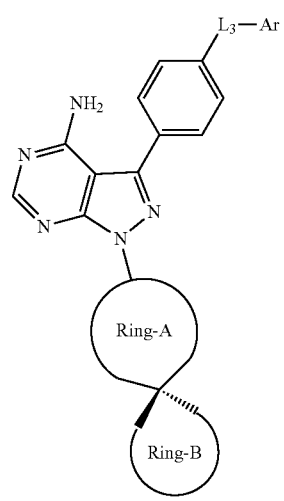

or a pharmaceutically acceptable salt, hydrate or solvate thereof, wherein:

may be selected from the group consisting of:

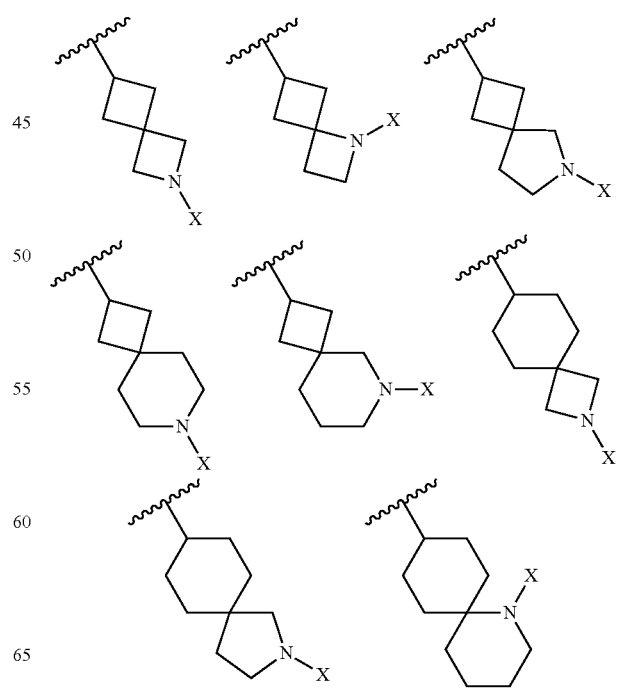

$R^e$ may be independently chosen from halogen, $C_{1-12}$alkyl, $C_{2-12}$alkenyl, $C_{2-12}$alkynyl, $C_{3-12}$ cycloalkyl, $C_{6-12}$aryl, a 3-12 membered heteroalicyclic ring, a 5-12 membered heteroaryl ring, $-S(O)_mR^d$, $-S(O)_2NR^dR^d$, $-S(O)_2OR^d$, $SF_5$, $-CN$, $-NO_2$, $-NR^dR^d$, $-(CR^6R^7)_nOR^d$, $-CN$, $-C(O)R^d$, $-OC(O)R^d$, $-O(CR^dR^d)_nR^d$, $-NR^dC(O)R^d$, $-(CR^dR^d)_nC(O)OR^4$, $-(CR^dR^d)_nOR^4$, $-(CR^dR^d)_nC(O)NR^dR^d$, $-(CR^dR^d)_nNCR^dR^d$, $-C(=NR^d)NR^dR^d$, $-NR^dC(O)NR^dR^d$, $-NR^dS(O)_2R^d$ or $-C(O)NR^dR^d$, wherein each hydrogen in $R^d$ may be unsubstituted or substituted by $R^f$; wherein two $R^d$ on the same atom may be unconnected or connected to form a carbocyclic ring, or two $R^d$ on the same atom may be unconnected or connected to form a carbocyclic ring in which one or more carbon ring atoms may be replaced with one or more O, S, S(O), S(O)$_2$, C(O), C(S) and NR$^d$;

n may be selected from 1 to 6;

$R^f$ may be independently chosen from halogen, $C_{1-12}$alkyl, $C_{2-12}$alkenyl, $C_{2-12}$alkynyl, $C_{3-12}$cycloalkyl, $C_{6-12}$aryl, a 3-12 membered heteroalicyclic ring, a 5-12 membered heteroaryl ring, $-NH_2$, $-CN$, $-OH$, $-O-C_{1-12}$alkyl, $-O-(CH_2)_nC_{3-12}$cycloalkyl, $-O-(CH_2)_nC_{6-12}$aryl, $-O-(CH_2)_n$(3-12 membered heteroalicyclic ring) or $-O-(CH_2)_n$(5-12 membered heteroaryl ring); and two $R^e$ on adjacent atoms may be unconnected or connected to form a $C_{6-12}$ aryl ring, a 5-12 membered heteroaryl ring, a $C_{5-20}$ cycloalkyl ring or a 5-20 membered heteroalicyclic ring, or two $R^e$ on adjacent atoms may be unconnected or connected or combined to form a $C_{6-12}$ aryl ring, a 5-12 membered heteroaryl ring, a $C_{5-20}$ cycloalkyl ring or a 5-20 membered heteroalicyclic ring which contains one or more heteroatom selected from O, NR$^d$, S.

The compound of the present invention may be:

1-(6-(4-Amino-3-(4-phenoxyphenyl)-1H-pyrazolo[3,4-d]pyrimidin-1-yl)-2-azaspiro[3.3]heptan-2-yl)prop-2-en-1-one;

1-(2-(4-amino-3-(4-phenoxyphenyl)-1H-pyrazolo[3,4-d]pyrimidin-1-yl)-7-azaspiro[3.5]nonan-7-yl)prop-2-en-1-one, 1-(7-(4-amino-3-(4-phenoxyphenyl)-1H-pyrazolo[3,4-d]pyrimidin-1-yl)-2-azaspiro[3.5]nonan-2-yl)prop-2-en-1-one; and 1-(2-(4-amino-3-(4-phenoxyphenyl)-1H-pyrazolo[3,4-d]pyrimidin-1-yl)-6-azaspiro[3.5]nonan-6-yl)prop-2-en-1-one.

According to another embodiment, there is provided a pharmaceutical composition comprising a compound of the present invention and a pharmaceutically acceptable carrier.

According to another embodiment, there is provided a pharmaceutical composition comprising a compound of the present invention in combination with an anti-cancer agent selected from cytotoxic agents, antimitotic agents, antimetabolites, proteasome inhibitors, HDAC inhibitors, a kinase inhibitor, or combination thereof.

According to another embodiment, there is provided a method of treating a disease or condition comprising administering a therapeutically effective amount of a compound the present invention to an individual in need thereof.

According to another embodiment, there is provided a method of treating a disease or condition comprising administering a therapeutically effective amount of a compound of the present invention together with radiotherapy to an individual in need thereof.

The disease or condition may be chosen from a bladder cancer, a brain cancer, a breast cancer, a uterus cancer, a chronic lymphoid leukemia, a colon cancer, an esophagus -continued X may be:

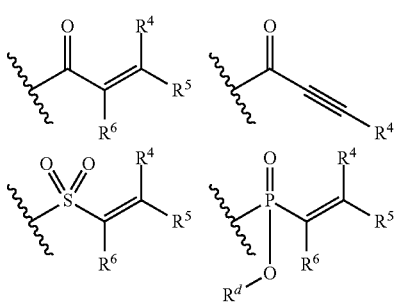

$R^5$, $R^4$ and $R^6$ may be independently selected from H, $C_{1-12}$alkyl, $C_{1-12}$heteroalkyl, $C_{1-12}$ heterocycloalkyl, $C_{2-12}$ alkenyl, $C_{2-12}$ alkynyl, $C_{3-12}$ cycloalkyl;

$L_3$ may be CH$_2$, O, S, NR$^d$;

$R^d$ may be H, $C_{1-6}$alkyl, $C_{3-6}$cycloalkyl, aryl or heteroaryl;

Ar may be an aryl or heteroaryl which may be unsubstituted or substituted with one or more $R^e$;

cancer, a liver cancer, a lymphoblastic leukemia, a follicular lymphoma, a melanoma, a malignant homeopathy, a myeloma, an ovarian cancer, a non-small-cell lung cancer, a prostate cancer, a small-cell lung cancer, and a lymphoid malignancy of B-cell origin.

The disease or condition may be chosen from an autoimmune disease, and an inflammatory disease.

The inflammatory disease may be chosen from an inflammatory bowel disease, an arthritis, a lupus, a rheumatoid arthritis, a psoriatic arthritis, an osteoarthritis, and a juvenile arthritis, a Still's disease, a diabetes, a myasthenia gravis, a Hashimoto's thyroiditis, an Ord's thyroiditis, a Graves' disease, a Sjogren's syndrome, a multiple sclerosis, a Guillain-Barre syndrome, an acute disseminated encephalomyelitis, an Addison's disease, an opsoclonus-myoclonus syndrome, an ankylosing spondylosis, an antiphospholipid antibody syndrome, an aplastic anemia, an autoimmune hepatitis, a coeliac disease, a Goodpasture's syndrome, an idiopathic thrombocytopenic purpura, an optic neuritis, a scleroderma, a primary biliary cirrhosis, a Reiter's syndrome, a Takayasu's arteritis, a temporal arteritis, a warm autoimmune hemolytic anemia, a Wegener's granulomatosis, a psoriasis, alopecia universalis, a Behcet's disease, a chronic fatigue, a dysautonomia, an endometriosis, an interstitial cystitis, a neuromyotonia, a scleroderma, a vulvodynia, a transplantation, a transfusion, an anaphylaxis, an allergy, a type I hypersensitivity, an allergic conjunctivitis, an allergic rhinitis, an atopic dermatitis, an asthma, an appendicitis, a blepharitis, a bronchiolitis, a bronchitis, a bursitis, a cervicitis, a cholangitis, a cholecystitis, a colitis, a conjunctivitis, a cystitis, a dacryoadenitis, a dermatitis, a dermatomyositis, an encephalitis, an endocarditis, an endometritis, an enteritis, an enterocolitis, an epicondylitis, an epididymitis, a fasciitis, a fibrositis, a gastritis, a gastroenteritis, a hepatitis, a hidradenitis suppurativa, a laryngitis, a mastitis, a meningitis, a myelitis myocarditis, a myositis, a nephritis, an oophoritis, an orchitis, an osteitis, an otitis, a pancreatitis, a parotitis, a pericarditis, a peritonitis, a pharyngitis, a pleuritis, a phlebitis, a pneumonitis, a pneumonia, a proctitis, a prostatitis, a pyelonephritis, a rhinitis, a salpingitis, a sinusitis, a stomatitis, a synovitis, a tendonitis, a tonsillitis, an uveitis, a vaginitis, a vasculitis, or a vulvitis.

The disease or condition may be a B-cell proliferative disorder chosen from a diffuse large B cell lymphoma, a follicular lymphoma, a chronic lymphocytic lymphoma, a chronic lymphocytic leukemia, a B-cell prolymphocytic leukemia, a lymphoplasmacytic lymphoma/Waldenstrom macroglobulinemia, a splenic marginal zone lymphoma, a plasma cell myeloma, a plasmacytoma, an extranodal marginal zone B cell lymphoma, a nodal marginal zone B cell lymphoma, a mantle cell lymphoma, a mediastinal (thymic) large B cell lymphoma, an intravascular large B cell lymphoma, a primary effusion lymphoma, a burkitt lymphoma/leukemia, or a lymphomatoid granulomatosis.

According to another embodiment, there is provided a use of a compound of the present invention, or the composition of the present invention for the treatment of a disease or condition.

According to another embodiment, there is provided a use of a compound of the present invention, or the composition of the present invention for the fabrication of a medicament for the treatment of a disease or condition.

The disease or condition may be chosen from a bladder cancer, a brain cancer, a breast cancer, a uterus cancer, a chronic lymphoid leukemia, a colon cancer, an esophagus cancer, a liver cancer, a lymphoblastic leukemia, a follicular lymphoma, a melanoma, a malignant homeopathy, a myeloma, an ovarian cancer, a non-small-cell lung cancer, a prostate cancer, a small-cell lung cancer, and a lymphoid malignancy of B-cell origin.

The disease or condition may be chosen from an autoimmune disease, and an inflammatory disease.

The inflammatory disease may be chosen from an inflammatory bowel disease, an arthritis, a lupus, a rheumatoid arthritis, a psoriatic arthritis, an osteoarthritis, a juvenile arthritis, a Still's disease, a diabetes, a myasthenia gravis, a Hashimoto's thyroiditis, an Ord's thyroiditis, a Graves' disease, a Sjogren's syndrome, a multiple sclerosis, a Guillain-Barre syndrome, an acute disseminated encephalomyelitis, an Addison's disease, an opsoclonus-myoclonus syndrome, an ankylosing spondylosis, an antiphospholipid antibody syndrome, an aplastic anemia, an autoimmune hepatitis, a coeliac disease, a Goodpasture's syndrome, an idiopathic thrombocytopenic purpura, an optic neuritis, a scleroderma, a primary biliary cirrhosis, a Reiter's syndrome, a Takayasu's arteritis, a temporal arteritis, a warm autoimmune hemolytic anemia, a Wegener's granulomatosis, a psoriasis, alopecia universalis, a Behcet's disease, a chronic fatigue, a dysautonomia, an endometriosis, an interstitial cystitis, a neuromyotonia, a scleroderma, a vulvodynia, a transplantation, a transfusion, an anaphylaxis, an allergy, a type I hypersensitivity, an allergic conjunctivitis, an allergic rhinitis, an atopic dermatitis, an asthma, an appendicitis, a blepharitis, a bronchiolitis, a bronchitis, a bursitis, a cervicitis, a cholangitis, a cholecystitis, a colitis, a conjunctivitis, a cystitis, a dacryoadenitis, a dermatitis, a dermatomyositis, an encephalitis, an endocarditis, an endometritis, an enteritis, an enterocolitis, an epicondylitis, an epididymitis, a fasciitis, a fibrositis, a gastritis, a gastroenteritis, a hepatitis, a hidradenitis suppurativa, a laryngitis, a mastitis, a meningitis, a myelitis myocarditis, a myositis, a nephritis, an oophoritis, an orchitis, an osteitis, an otitis, a pancreatitis, a parotitis, a pericarditis, a peritonitis, a pharyngitis, a pleuritis, a phlebitis, a pneumonitis, a pneumonia, a proctitis, a prostatitis, a pyelonephritis, a rhinitis, a salpingitis, a sinusitis, a stomatitis, a synovitis, a tendonitis, a tonsillitis, an uveitis, a vaginitis, a vasculitis, or a vulvitis.

The disease or condition may be a B-cell proliferative disorder chosen from a diffuse large B cell lymphoma, a follicular lymphoma, a chronic lymphocytic lymphoma, a chronic lymphocytic leukemia, a B-cell prolymphocytic leukemia, a lymphoplasmacytic lymphoma/Waldenstrom macroglobulinemia, a splenic marginal zone lymphoma, a plasma cell myeloma, a plasmacytoma, an extranodal marginal zone B cell lymphoma, a nodal marginal zone B cell lymphoma, a mantle cell lymphoma, a mediastinal (thymic) large B cell lymphoma, an intravascular large B cell lymphoma, a primary effusion lymphoma, a burkitt lymphoma/leukemia, or a lymphomatoid granulomatosis.

Abbreviations used herein have their conventional meaning within the chemical and biological arts.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl". The said alkyl is optionally substituted with one or more halogen atom(s).

The term "Fluoroalkyl" means alkyl as defined above wherein one or more hydrogen atoms have been replaced by fluorine atoms.

The term "Alkylene" by itself or as part of another substituent means a divalent radical derived from an alkyl, as exemplified, but not limited, by —$CH_2CH_2CH_2CH_2$—, —$CH_2CH$=$CHCH_2$—, —$CH_2C$≡$CCH_2$—, $CH_2CH_2CH$($CH_2CH_2CH_3$)$CH_2$—. Typically, an alkyl (or alkylene) group has from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The said alkylene is optionally substituted with one or more halogen atom(s).

The term "Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like. The said alkynyl is optionally substituted with one or more halogen atom(s).

The term "Cycloalkyl" means mono- or bicyclic saturated carbocyclic rings, each of which has from 3 to 10 carbon atoms. A "fused analog" of cycloalkyl means a monocyclic rings fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, and the like. The said cycloalkyl is optionally substituted with one or more halogen atom(s).

The term "Alkoxy" means alkoxy groups of a straight or branched having the indicated number of carbon atoms. $C_{1-6}$alkoxy, for example, includes methoxy, ethoxy, propoxy, isopropoxy, and the like.

The term "Heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedi-oxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The term "Cycloalkoxy" means cycloalkyl as defined above bonded to an oxygen atom, such as cyclopropyloxy.

The term "Fluoroalkoxy" means alkoxy as defined above wherein one or more hydrogen atoms have been replaced by fluorine atoms.

The term "Aryl" means mono- or bicyclic aromatic rings containing only carbon atoms. A "fused analog" of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,4-benzodioxanyl, and the like.

The term "Heteroaryl" means a mono- or bicyclic aromatic ring containing at least one heteroatom selected from N, O and S, with each ring containing 5 to 6 atoms. A "fused analog" of heteroaryl means a heteroaryl group fused to a monocyclic cycloalkyl or monocyclic heterocyclyl group in which the point of attachment is on the aromatic portion. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

The said alkyl groups, aryl groups and said heteroaryl groups referred to in the definitions are unsubstituted or are substituted by at least one substituent selected from the group consisting of substituents.

The said substituents are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent-x groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, —SF$_5$, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

The term "Heterocyclyl" means mono- or bicyclic saturated rings containing at least one heteroatom selected from N, S and O, each of said ring having from 3 to 10 atoms in which the point of attachment may be carbon or nitrogen. A "fused analog" of heterocyclyl means a monocyclic heterocycle fused to an aryl or heteroaryl group in which the point of attachment is on the non-aromatic portion. Examples of "heterocyclyl" and fused analogs thereof include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1 H,3H)-pyrimidine-2,4-diones (N-substituted uracils).

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrugs may also have improved solubility in pharmaceutical compositions over the parent drug. An example, without limitation, of a prodrug would be a compound of any of Formula I, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Optical Isomers-Diastereomers-Geometric Isomers-Tautomers:

Compounds of Formula (A) may contain one or more asymmetric centers and may thus occur as racemates and racemic mixtures, single enantiomers, diastereomeric mixtures and individual diastereomers. The present invention is meant to comprehend all such isomeric forms of the compounds of Formula (A).

Some of the compounds described herein contain olefinic double bonds, and unless specified otherwise, are meant to include both E and Z geometric isomers.

Some of the compounds of Formula (A) may contain one or more than one cyclic ring systems and may thus exist in cis- and trans-isomers. The present invention is meant to include all such cis- and trans-isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula (A).

Compounds of the Formula (A) may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine or acid as a resolving agent or on a chiral HPLC column.

Alternatively, any enantiomer of a compound of the general Formula (A) may be obtained by stereospecific synthesis using optically pure starting materials or reagents of known configuration.

Stable Isotope-Labeled Analogs: One or more than one of the protons in compounds of Formula (A) can be replaced with deuterium atom(s), thus providing deuterated analogs that may have improved pharmacological activities.

Salts and Formulation

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydramine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is alkaline, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula (A) are meant to also include the pharmaceutically acceptable salts.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethy-cellulose, sodium alginate, polyvinyl-pyrrolidone, gum tragacanth and gum *acacia*; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an I atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns).

This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from log to 20 mg of the compound of the invention per actuation and the actuation volume may vary from 1 l to 100 l. A typical formulation may comprise a compound of Formula (A) propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 fig to 10 mg of the compound of Formula (A). The overall daily dose will typically be in the range 1 lag to 10 mg which may be administered in a single dose or, more usually, as divided doses throughout the day.

Compounds of Formula (A) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula (A) are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Utilities

The compounds of the present invention are useful for treating diseases associated with abnormal activities of BTK.

The present invention also comprises methods of treating diseases in a patient by using methods includes administering to the patient a therapeutically effective amount of a compound having Formula (A).

More especially, the compounds according to the invention will be useful in the treatment of diseases of abnormal cell growth and/or dysregulated apoptosis, such as mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination thereof. Still another embodiment includes methods of treating mesothioloma, bladder cancer, pancreatic cancer, skin cancer, cancer of the head or neck, cutaneous or intraocular melanoma, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination of one or more of the above cancers in a patient, the methods including administering thereto a therapeutically effective amount of a compound having Formula (A).

The compounds of Formula (A) are also useful for treatment of autoimmune diseases and inflammatory diseases, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjogren's syndrome, multiple sclerosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, vulvodynia, transplantation, transfusion, anaphylaxis, allergy, type I hypersensitivity, allergic conjunctivitis, allergic rhinitis, or atopic dermatitis, asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In yet another aspect of the present invention, there is provided a method for treating a cancer by administering to a subject in need thereof a composition containing a therapeutically effective amount of at least one compound having the structure of any of the compounds of Formula (A).

In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis.

In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In another aspect, provided herein is a method for treating a thromboembolic disorder by administering to a subject in need thereof a composition containing a therapeutically effective amount of at least one compound having the structure of any of Formula (A). In some embodiments, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

The present invention relates also to pharmaceutical compositions including at least one compound of Formula (A) on its own or in combination with one or more pharmaceutically acceptable excipients.

Among the pharmaceutical compositions according to the invention there may be mentioned more especially those that are suitable for oral, parenteral, nasal, per- or transcutaneous, rectal, perlingual, ocular or respiratory administration, especially tablets or dragees, sublingual tablets, sachets, packets, gelatin capsules, glossettes, lozenges, suppositories, creams, ointments, dermal gels, and drinkable or injectable ampoules.

The dosage varies according to the sex, age and weight of the patient, the route of administration, the nature of the therapeutic indication, or any associated treatments, and ranges from 0.01 mg to 1 g per 24 hours in one or more administrations.

Moreover, the present invention relates also to the combination of a compound of Formula (A), or Formula (B), with one or more anticancer agents selected from cytotoxic agents, mitotic poisons, anti-metabolites, proteasome inhibitors and kinase inhibitors, and to the use of that type of combination in the manufacture of medicaments for use in the treatment of cancer.

The compounds of the invention may also be used in combination with radiotherapy in the treatment of cancer.

Compounds having Formula (A) are also expected to be useful as chemotherapeutic agents in combination with therapeutic agents that include, but are not limited to, angiogenesis inhibitors, antiproliferative agents, other kinase inhibitors, other receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunomodulators, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs, MEK inhibitors, CDK inhibitors, ErbB2 receptor inhibitors, mTOR inhibitors, Bcl inhibitors, Mcl inhibitors and combinations thereof as well as other antitumor agents.

Angiogenesis inhibitors include, but are not limited to, EGFR inhibitors, PDGFR inhibitors, VEGFR inhibitors, TIE2 inhibitors, IGFIR inhibitors, matrix metalloproteinase 2 (MMP-2) inhibitors, matrix metalloproteinase 9 (MMP-9) inhibitors, thrombospondin analogs such as thrombospondin-1 and N-Ac-Sar-Gly-Val-D-allolle-Thr-Nva-He-Arg-Pro-NHCH$_2$CH$_3$ or a salt thereof and analogues of N-Ac-Sar-Gly-Val-D-allolle-Thr-Nva-Ile-Arg-PrO-NHCH$_2$CH$_3$ such as N-Ac-GlyVal-D-aIle-Ser-Gln-Ile-Arg-ProNHCH$_2$CH$_3$ or a salt thereof.

Examples of EGFR inhibitors include, but are not limited to, Iressa (gefitinib), Tarceva (erlotinib or OSI-774), Icotinib, Erbitux (cetuximab), EMD-7200, ABX-EGF, HR3, IgA antibodies, TP-38 (IVAX), EGFR fusion protein, EGF-vaccine, anti-EGFr immunoliposomes and Tykerb (lapatinib).

Examples of PDGFR inhibitors include, but are not limited to, CP-673,451 and CP-868596.

Examples of VEGFR inhibitors include, but are not limited to, Avastin (bevacizumab), Sutent (sunitinib, SUI 1248), Nexavar (sorafenib, BAY43-9006), regorafenib, CP-547,632, axitinib (AG13736), Apatinib, cabozantinib, Zactima (vandetanib, ZD-6474), AEE788, AZD-2171, VEGF trap, Vatalanib (PTK-787, ZK-222584), Macugen, M862, Pazopanib (GW786034), BC-00016, ABT-869 and angiozyme.

Examples of thrombospondin analogs include, but are not limited to, ABT-510.

Examples of BCL inhibitors include, but not limited to, obatoclax and navitoclax, ABT199.

Examples of aurora kinase inhibitors include, but are not limited to, VX-680, AZD-1152 and MLN-8054. Example of polo-like kinase inhibitors include, but are not limited to, BI-2536.

Examples of bcr-abl kinase inhibitors include, but are not limited to, Gleevec (imatinib), ponatinib nilotinib and Dasatinib (BMS354825).

Examples of platinum containing agents includes, but are not limited to, cisplatin, Paraplatin (carboplatin), eptaplatin, lobaplatin, nedaplatin, Eloxatin (oxaliplatin) or satraplatin.

Examples of mTOR inhibitors includes, but are not limited to, CCI-779, rapamycin, temsirolimus, everolimus, RAD001, INK-128 and ridaforolimus.

Examples of HSP-90 inhibitors includes, but are not limited to, geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

Examples of histone deacetylase inhibitors (HDAC) includes, but are not limited to, Suberoylanilide hydroxamic acid (SAHA), MS-275, valproic acid, TSA, LAQ-824, Trapoxin, tubacin, tubastatin, ACY-1215 and Depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991 and AZD-5438.

Examples of COX-2 inhibitors include, but are not limited to, CELEBREX™ (celecoxib), parecoxib, deracoxib, ABT-963, MK-663 (etoricoxib), COX-189 Lumiracoxib), BMS347070, RS 57067, NS-398, Bextra (valdecoxib), paracoxib, Vioxx (rofecoxib), SD-8381, 4-Methyl-2-(3,4-dimethylphenyl)-l-(4-sulfamoyl-phenyl-1H-pyrrole, T-614, JTE-522, S-2474, SVT-2016, CT-3, SC-58125 and Arcoxia (etoricoxib).

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol) and Oxaprozin (Daypro).

Examples of ErbB2 receptor inhibitors include, but are not limited to, CP-724-714, CI-1033, (canertinib), Herceptin (trastuzumab), Omitarg (2C4, petuzumab), TAK-165, GW-572016 (lonafarnib), GW-282974, EKB-569, PI-166, dHER2 (HER2 Vaccine), APC8024 (HER2 Vaccine), anti-HER/2neu bispecific antibody, B7.her2IgG3, AS HER2 trifunctional bispecfic antibodies, mAB AR-209 and mAB 2B-1.

Examples of alkylating agents include, but are not limited to, nitrogen mustard N-oxide, cyclophosphamide, ifosfamide, trofosfamide, Chlorambucil, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, uracil analogues such as 5-fluorouracil (5-FU) alone or in combination with leucovorin, tegafur, UFT, doxifluridine, carmofur, cytarabine, cytarabine, enocitabine, S-I, Alimta (premetrexed disodium, LY231514, MTA), Gemzar (gemcitabine), fludarabine, 5-azacitidine, capecitabine, cladribine, clofarabine, decitabine, eflornithine, ethnylcytidine, cytosine arabinoside, hydroxyurea, TS-I, melphalan, nelarabine, nolatrexed, ocfosate, disodium premetrexed, pentostatin, pelitrexol, raltitrexed, triapine, trimetrexate, vidarabine, vincristine, vinorelbine, mycophenolic acid, tiazofurin, Ribavirin, EICAR, hydroxyurea and deferoxamine.

Examples of antibiotics include intercalating antibiotics but are not limited to, aclarubicin, actinomycins such as actinomycin D, amrubicin, annamycin, adriamycin, bleomycin a, bleomycin b, daunorubicin, doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, diflomotecan, irinotecan HCL (Camptosar), edotecarin, epirubicin (Ellence), etoposide, exatecan, gimatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab, Bevacizumab, Trastuzimab, specific CD40 antibodies and specific IGFIR antibodies.

Examples of hormonal therapies include, but are not limited to, exemestane (Aromasin), leuprolide acetate, anastrozole (Arimidex), fosrelin (Zoladex), goserelin, doxercalciferol, fadrozole, formestane, tamoxifen citrate (tamoxifen), Casodex, Abarelix, Trelstar, finasteride, fulvestrant, toremifene, raloxifene, lasofoxifene, letrozole, flutamide, bicalutamide, megesterol, mifepristone, nilutamide, dexamethasone, predisone and other glucocorticoids.

Examples of retinoids/deltoids include, but are not limited to, seocalcitol (EB 1089, CB 1093), lexacalcitrol (KH 1060), fenretinide, Aliretinoin, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MGI 32, NPI-0052 and PR-171.

Examples of immunologicals include, but are not limited to, interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-nl and combinations thereof. Other agents include filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFGI), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofrran, picibanil and ubenimex.

Examples of pyrimidine analogs include, but are not limited to, 5-Fluorouracil, Floxuridine, Doxifluridine, Ratitrexed, cytarabine (ara C), Cytosine arabinoside, Fludarabine, and Gemcitabine.

Examples of purine analogs include, but are not limited to, Mercaptopurine and thioguanine.

Examples of immunomodulators include but not limited to, thalidomide and lenalidomide.

Examples of antimitotic agents include, but are not limited to, paclitaxel, docetaxel, ABRAXANE, epothilone D (KOS-862) and ZK-EPO.

Synthesis
The compounds of the present invention may be prepared according to the following synthetic schemes:
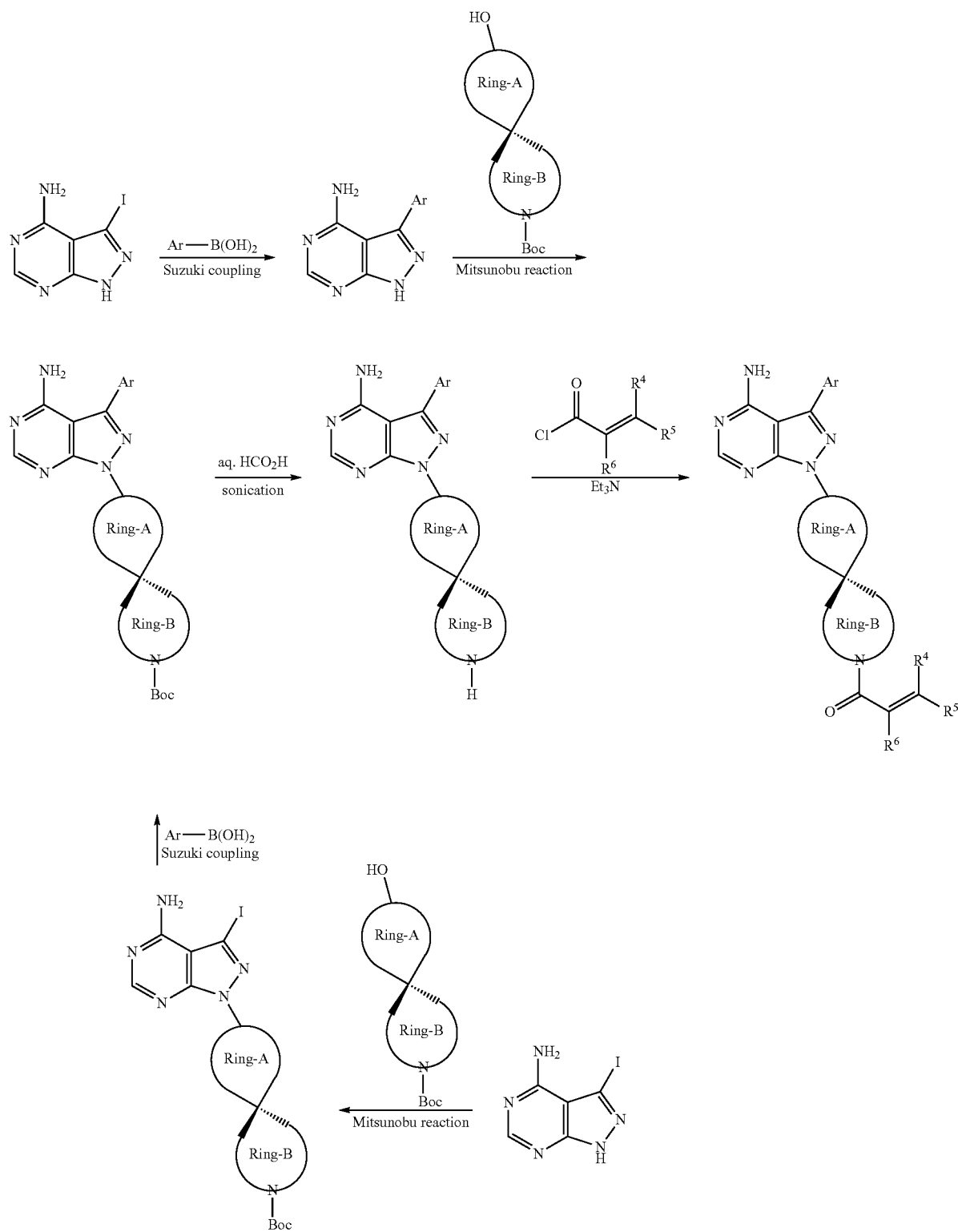
Scheme 1

Scheme 2
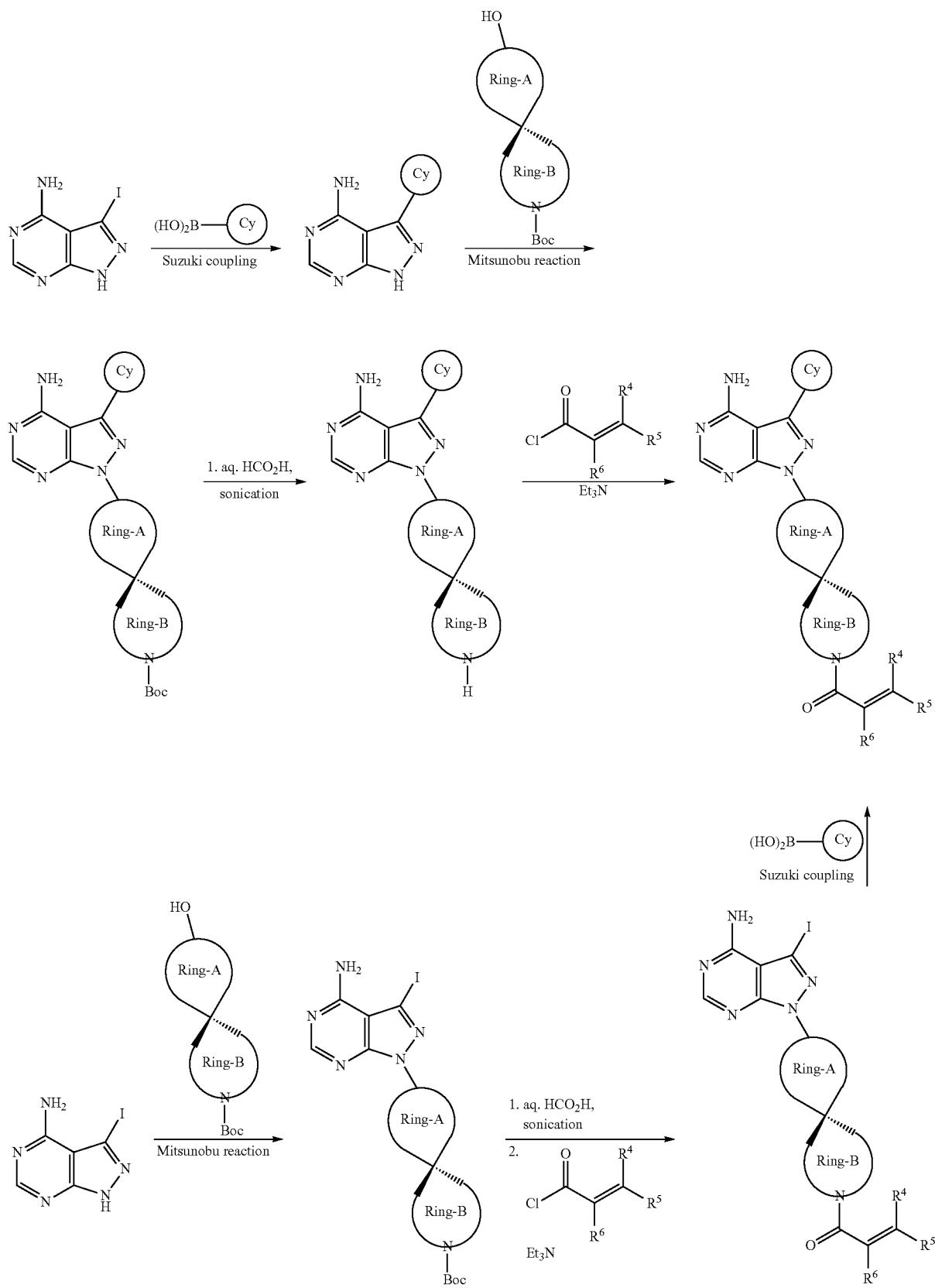

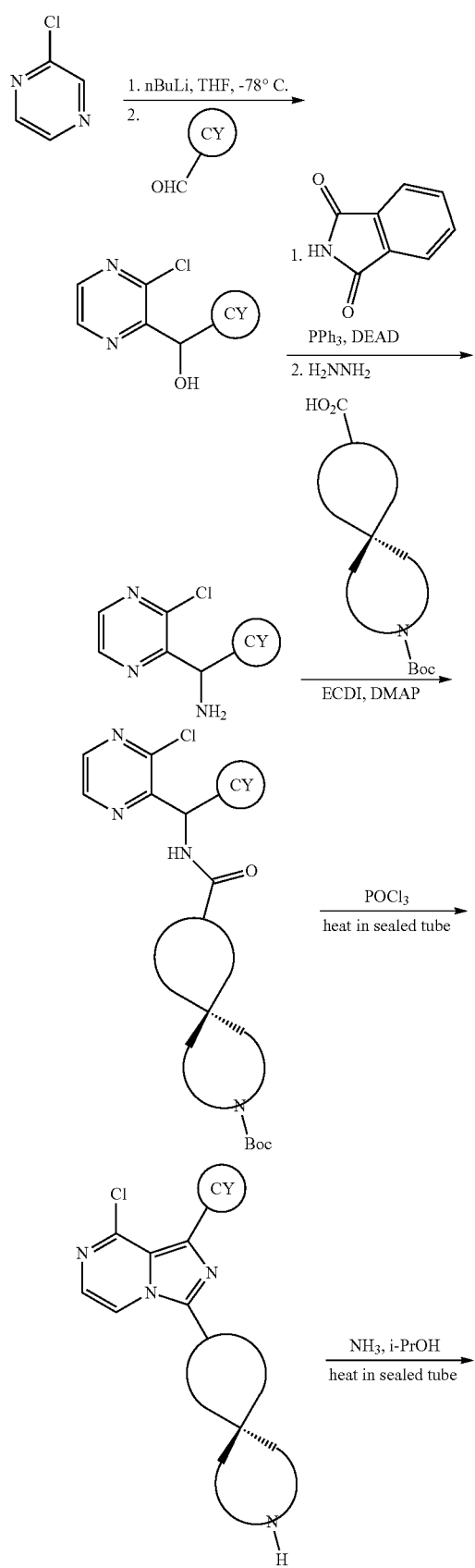
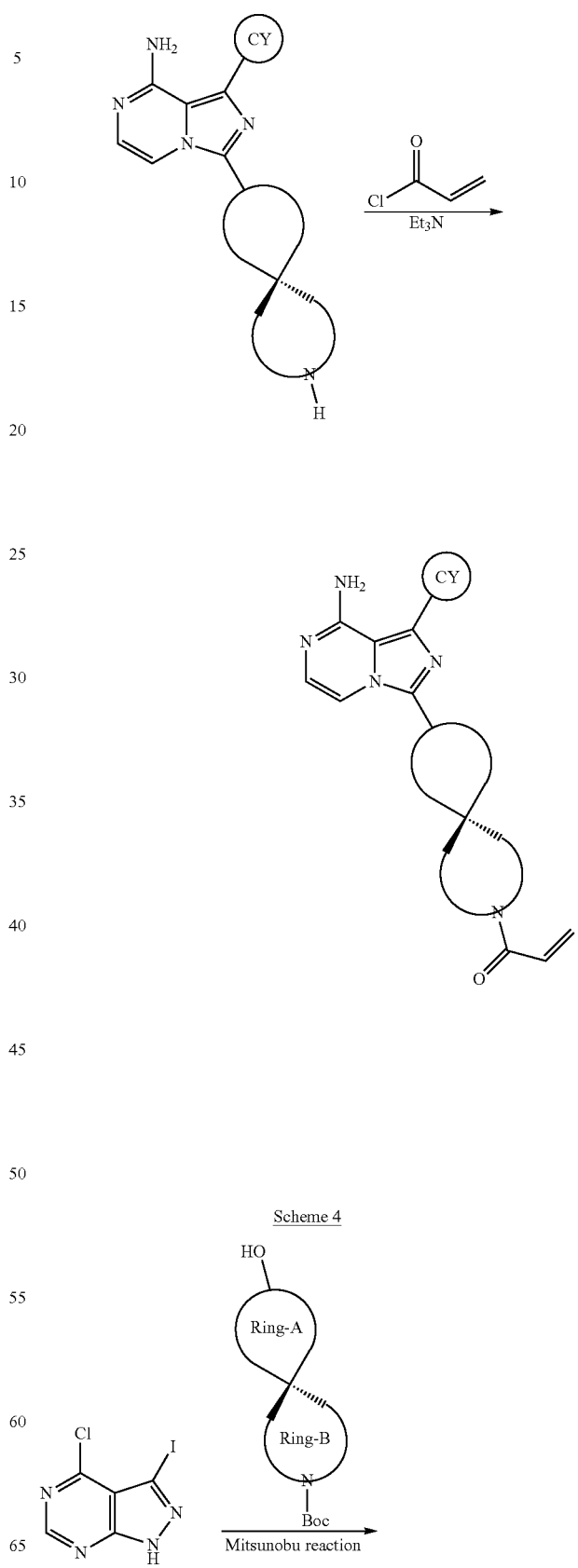

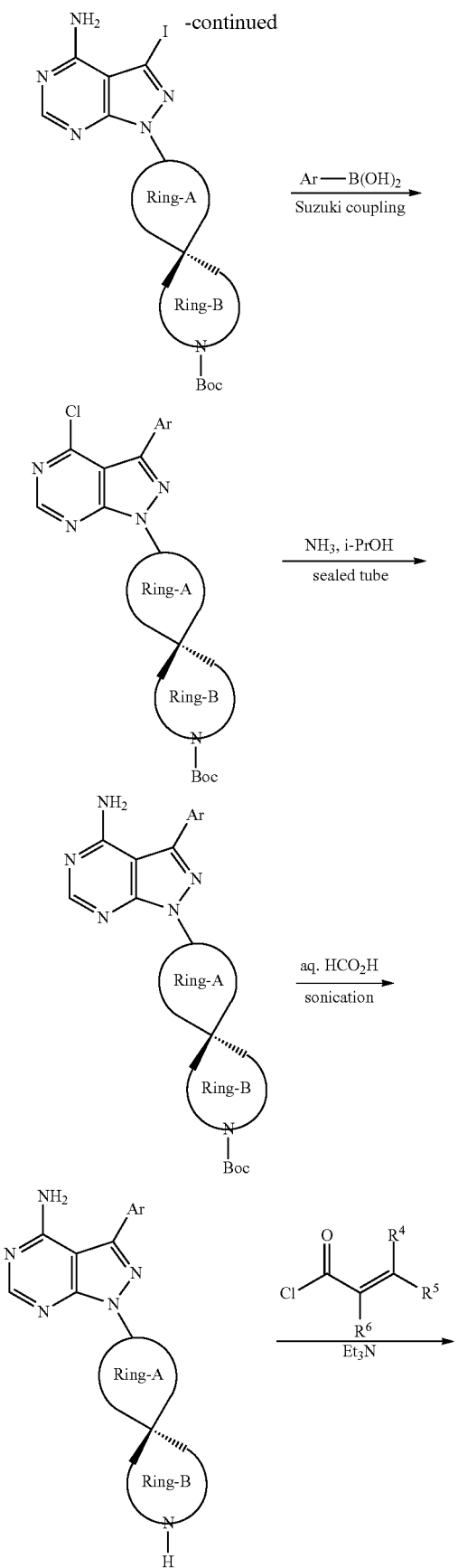

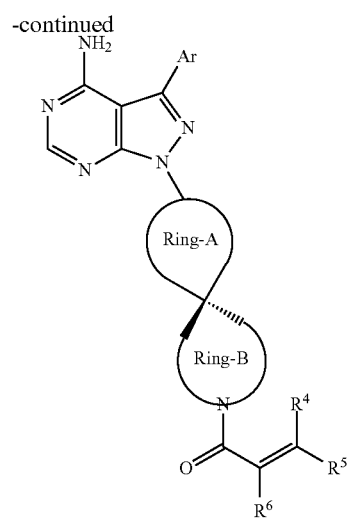

Compounds of the present invention may be made by synthetic chemical processes, examples of which are shown herein below. It is meant to be understood that the order of the steps in the processes may be varied, that reagents, solvents and reaction conditions may be substituted for those specifically mentioned, and that vulnerable moieties may be protected and deprotected, as necessary.

The following abbreviations have the meanings indicated. DBU means I,8-diazabicyclo[5.4.0]undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means I,2-bis(dimethylphosphino)ethane; DMSO means dimethylsulfoxide; dppb means I,4-bis(diphenylphosphino)butane; dppe means 1,2-bis(diphenylphosphino)ethane; dppf means I,r-bis(diphenylphosphino)ferrocene; dppm means I,I-bis(diphenylphosphino)methane; DIAD means diisopropylazodicarboxylate; EDCI means I-(3-dimethylaminopropyl)-3-ethylcarbodiimide; HATU means 0-(7-azabenzotriazol-1-yl)-N,NTSr'N'-tetramethyluronium hexafluorophosphate; HMPA means hexamethyiphosphorarnide; IPA means isopropyl alcohol; LDA means lithium diisopropylamide; LHMDS means lithium bis(hexamethyldisilylamide); LAH means lithium aluminum hydride; NCS means N-chlorosuccinimide; PyBOP means benzotriazol-1-yloxytripyrrolidinophosphonium hexafluorophosphate; TDA-I means tris(2-(2-methoxyethoxy)ethyl)amine; DCM means dichloromethame; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine; rt means room temperature.

The following preparations and examples illustrate the invention but do not limit it in any way.

Features and advantages of the subject matter hereof will become more apparent in light of the following detailed description of selected embodiments. As will be realized, the subject matter disclosed and claimed is capable of modifications in various respects, all without departing from the scope of the claims. Accordingly, the description is to be regarded as illustrative in nature, and not as restrictive and the full scope of the subject matter is set forth in the claims.

DETAILED DESCRIPTION

The present invention provides novel cyclic molecules and methods of preparing and potential therapeutic uses of these novel compounds. The inventive compounds may be useful in the treatment of B cell lymphoma, leukemia and autoimmune disorders.

The present invention provides compounds of any of Formula (A), which are useful as BTK inhibitors.

In one aspect are compounds of Formula (A), pharmaceutically acceptable salts, pharmaceutically active metabolites, pharmaceutically acceptable prodrugs, and pharmaceutically acceptable solvates thereof.

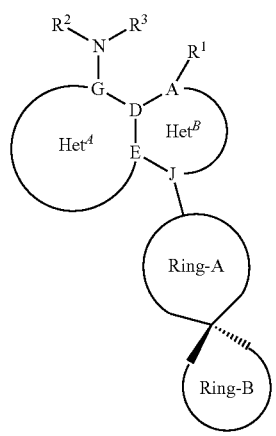

Formula (A)

or a pharmaceutically acceptable salt, hydrate or solvate thereof, wherein:

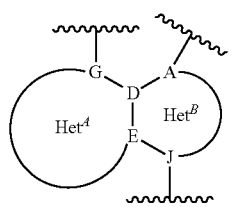

is selected from the following moieties:

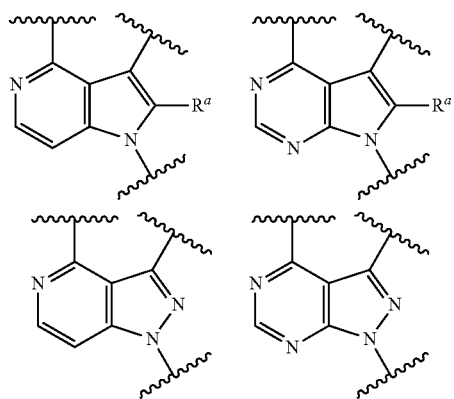

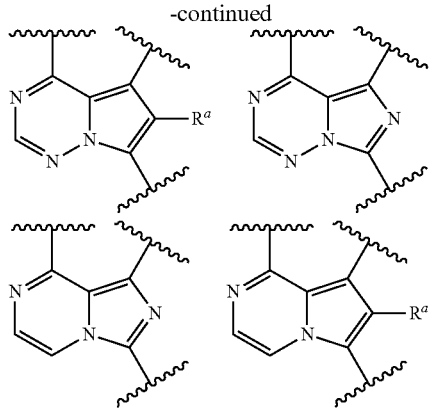

$R^a$ is H, halogen, $L_1$-(substituted or unsubstituted $C_1$-$C_3$ alkyl), $L_1$-(substituted or unsubstituted $C_2$-$C_3$ alkenyl), $L_1$-(substituted or unsubstituted heteroaryl), or $L_1$-(substituted or unsubstituted aryl), wherein $L_1$ is a bond, O, S, —S(=O), S(=O)$_2$, S(=O)$_2$—NH, NH, C(O), —NHC(O)O, —OC(O)NH, —NHC(O), or —C(O)NH;

$R^1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), $L_2$-(substituted or unsubstituted aryl)-$L_2$-(substituted or unsubstituted aryl), $L_2$-(substituted or unsubstituted aryl)-$L_2$-(substituted or unsubstituted heteroaryl), $L_2$-(substituted or unsubstituted heteroaryl)-$L_2$-(substituted or unsubstituted aryl), $L_2$-(substituted or unsubstituted heteroaryl)-$L_2$-(substituted or unsubstituted heteroaryl), wherein $L_2$ is a bond, O, S, —S(=O), —S(=O)$_2$, C(=O), -(substituted or unsubstituted $C_1$-$C_5$alkyl), or -(substituted or unsubstituted $C_2$-$C_5$alkenyl);

$R^2$ and $R^3$ are independently selected from H, $C_1$-$C_8$ alkyl and substituted $C_1$-$C_8$ alkyl;

Ring A is a 3 to 12 membered carbocyclic ring; or

Ring A is a 3 to 12 membered carbocyclic ring in which one or more carbon ring atoms are replaced with one or more O, S, —C(O)—, —C(S)—, NR$^c$, or Ring A is a 3 to 12 membered carbocyclic ring which unsubstituted or substituted with one or more R$^c$; or Ring A is a 3 to 12 membered carbocyclic ring in which one carbon ring atoms is replaced with a nitrogen atom and the nitrogen atom in Ring A is connected with J when J is a carbon atom;

R$^c$ is independently chosen from halogen, $C_{1-12}$alkyl, $C_{2-12}$ alkenyl, $C_{2-12}$ alkynyl, $C_{3-12}$ cycloalkyl, $C_{6-12}$ aryl, a 3-12 membered heteroalicyclic ring, a 5-12 membered heteroaryl ring, —NH$_2$, —CN, —OH, —O—(CH$_2$)$_n$C$_{3-12}$cycloalkyl, —O—(CH$_2$)$_n$C$_{6-12}$aryl, —O—(CH$_2$)$_n$(3-12 membered heteroalicyclic ring) or —O—(CH$_2$)$_n$(5-12 membered heteroaryl ring), with the proviso that when R$^c$ is halogen, —CN, —OH, —O—C$_{1-12}$alkyl, —O—(CH$_2$)$_n$C$_{3-12}$cycloalkyl, —O—(CH$_2$)$_n$C$_{6-12}$aryl, —O—(CH$_2$)$_n$(3-12 membered heteroalicyclic ring) or —O—(CH$_2$)$_n$(5-12 membered heteroaryl ring), R$^c$ is connected to an atom different than nitrogen, Ring B is a 3 to 12 membered carbocyclic ring; or Ring B is a 3 to 12 membered carbocyclic ring in which one or more carbon ring atoms are replaced with one or more O, S, S(O), S(O)$_2$, C(O), C(S), N—X; or Ring B is a 3 to 12 membered carbocyclic ring which is unsubstituted or substituted by X, —NR$^d$—X or C$_1$-C$_6$alkyl-NR$^d$X;

R$^d$ is H, C$_{1-6}$alkyl, C$_{3-6}$cycloalkyl, aryl or heteroaryl;

X is:

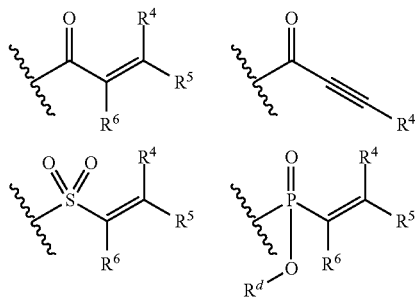

R$^5$, R$^4$ and R$^6$ are independently selected from among H, C$_{1-12}$alkyl, C$_{1-12}$heteroalkyl, C$_{1-12}$heterocycloalkyl, C$_{2-12}$ alkenyl, C$_{2-12}$ alkynyl, C$_{3-12}$ cycloalkyl;

n is selected from 1 to 6.

In another embodiment, the invention provides a compound of Formula (B) the following structure:

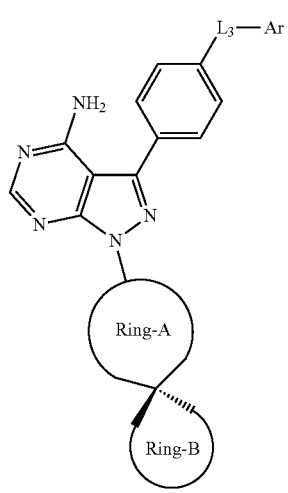

Formula (B)

or a pharmaceutically acceptable salt, hydrate or solvate thereof, wherein

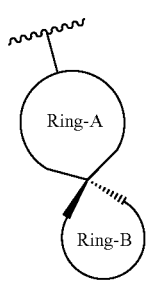

is selected from the group consisting of:

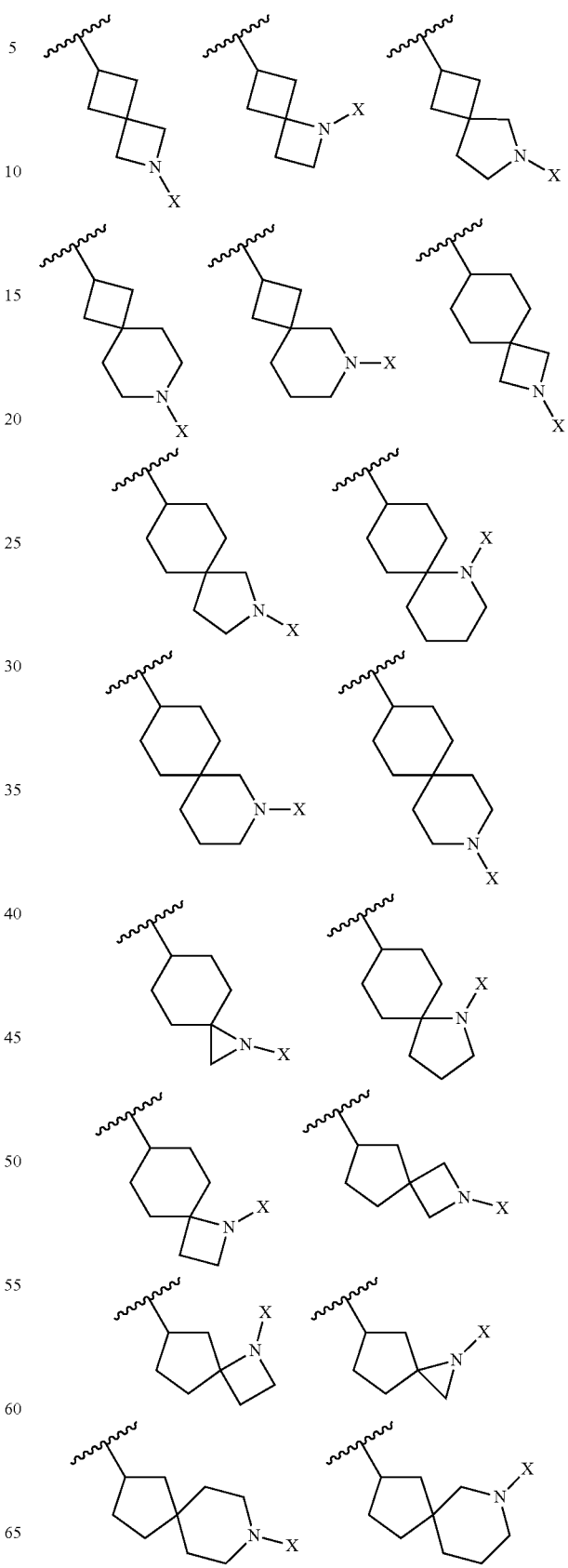

-continued

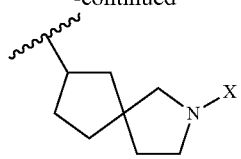

X is:

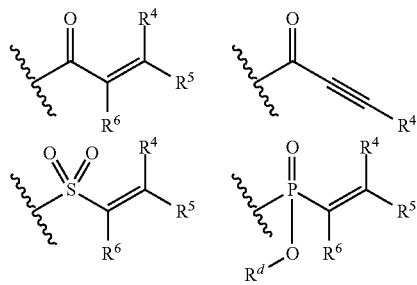

$R^5$, $R^4$ and $R^6$ are independently selected from among H, $C_{1-12}$heteroalkyl, $C_{1-12}$heterocycloalkyl, $C_{2-12}$ alkenyl, $C_{2-12}$ alkynyl, $C_{3-12}$ cycloalkyl;

$L_3$ is $CH_2$, O, S, $NR^d$, $R^d$ is H, $C_{1-6}$alkyl, $C_{3-6}$cycloalkyl, aryl or heteroaryl;

Ar is an aryl or heteroaryl which is optionally substituted with one or more $R^e$;

$R^e$ is independently halogen, $C_{1-12}$ alkyl, $C_{2-12}$ alkenyl, $C_{2-12}$ alkynyl, $C_{3-12}$ cycloalkyl, $C_{6-12}$ aryl, a 3-12 membered heteroalicyclic ring, a 5-12 membered heteroaryl ring, —S(O)$_m$R$^d$, —S(O)$_2$NR$^d$R$^d$, —S(O)$_2$OR$^d$, SF$_5$, —CN, —NO$_2$, —NR$^d$R$^d$, —(CR$^6$R$^7$)$_n$OR$^d$, —CN, —C(O)R$^d$, —OC(O)R$^d$, —O(CR$^d$R$^d$)$_n$R$^d$, —NR$^d$C(O)R$^d$, —(CR$^d$R$^d$)$_n$C(O)OR$^4$, —(CR$^d$R$^d$)$_n$OR$^4$, —(CR$^d$R$^d$)$_n$C(O)NR$^d$R$^d$, —(CR$^d$R$^d$)$_n$NCR$^d$R$^d$, —C(=NR$^d$)NR$^d$R$^d$, —NR$^d$C(O) NR$^d$R$^d$, —NR$^d$S(O)$_2$R$^d$ or —C(O)NR$^d$R$^d$, each hydrogen in $R^d$ is optionally substituted by $R^f$;

Two $R^d$ on the same atom can be connected to form a carbocyclic ring in which one or more carbon ring atoms are optionally replaced with one or more O, S, S(O), S(O)$_2$, C(O), C(S) and NR$^d$;

n is selected from 1 to 6;

$R^f$ is independently halogen, $C_{1-12}$ alkyl, $C_{2-12}$ alkenyl, $C_{2-12}$ alkynyl, $C_{3-12}$ cycloalkyl, $C_{6-12}$ aryl, a 3-12 membered heteroalicyclic ring, a 5-12 membered heteroaryl ring, —NH$_2$, —CN, —OH, —O—$C_{1-12}$alkyl, —O—(CH$_2$)$_n$C$_{3-12}$cycloalkyl, —O—(CH$_2$)$_n$C$_{6-12}$ aryl, —O—(CH$_2$)$_n$(3-12 membered heteroalicyclic ring) or —O—(CH$_2$)$_n$(5-12 membered heteroaryl ring);

two $R^e$ on adjacent atoms are unconnected or connected to form a $C_{6-12}$ aryl, a 5-12 membered heteroaryl ring, $C_{5-20}$ cycloalkyl or a 5-20 membered heteroalicyclic ring which may contain one or more heteroatom(s) such as O, NR$^d$, S;

In another embodiment, the invention provides stable isotope-labeled compounds of Formula (A).

In another embodiment, the invention provides prodrugs of the compounds of Formula (A).

In another embodiment, the invention provides the compounds having the following structures in Table 1 and Table 2:

TABLE 1

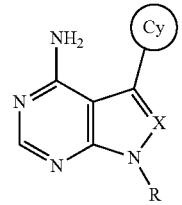

| | R | X |
|---|---|---|
| 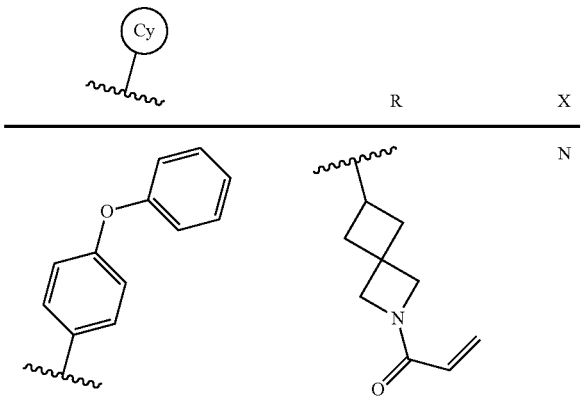 | | |

TABLE 1-continued
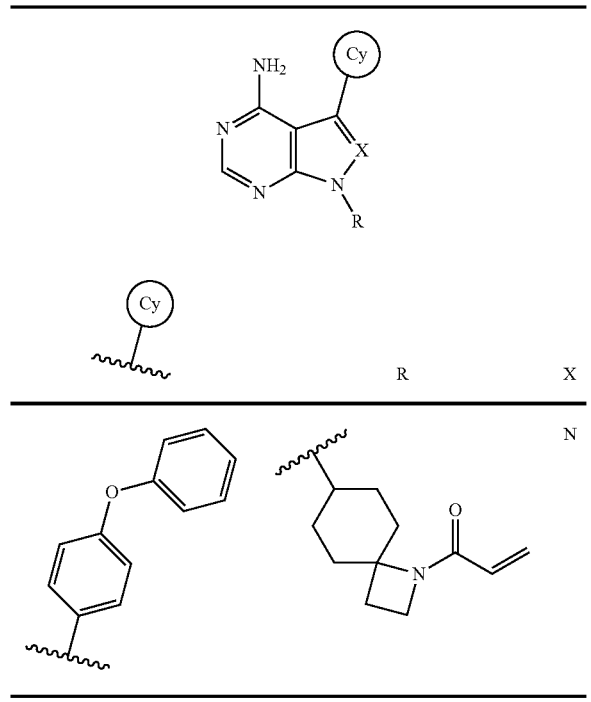
TABLE 2
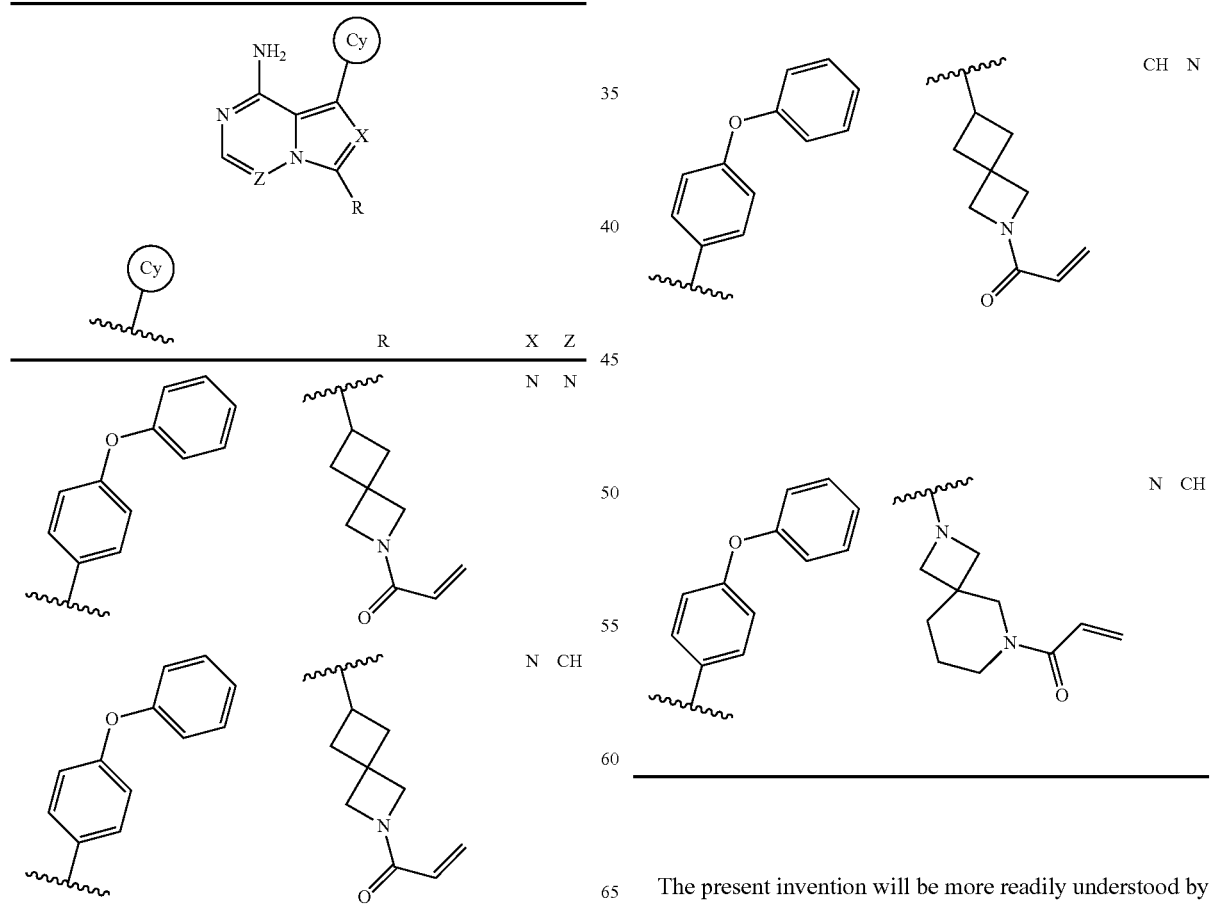
TABLE 2-continued
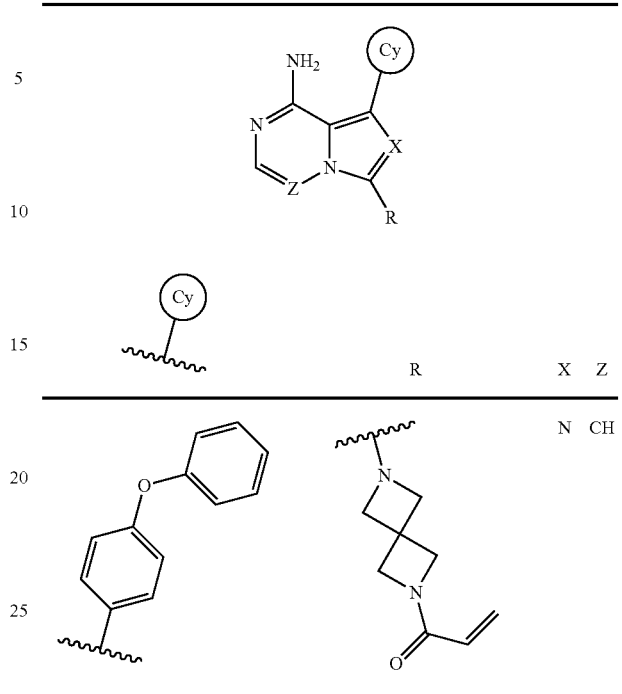
The present invention will be more readily understood by referring to the following examples which are given to illustrate the invention rather than to limit its scope.

EXAMPLE 1

1-(6-(4-Amino-3-(4-phenoxyphenyl)-1H-pyrazolo[3,4-d]pyrimidin-1-yl)-2-azaspiro[3.3]heptan-2-yl)prop-2-en-1-one

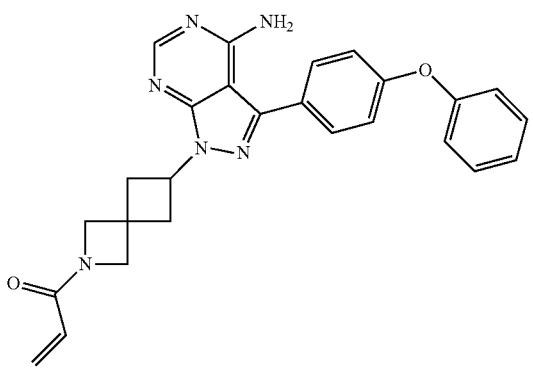 [SMILES: C=CC(=O)N1CC2(CC(n3nc(-c4ccc(Oc5ccccc5)cc4)c4c(N)ncnc43)C2)C1]

Step 1: 3-(4-phenoxyphenyl)-1H-pyrazolo[3,4-d]pyrimidin-4-amine

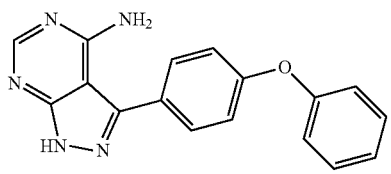 [SMILES: Nc1ncnc2[nH]nc(-c3ccc(Oc4ccccc4)cc3)c12]

To a mixture of 3-iodo-1H-pyrazolo[3,4-d]pyrimidin-4-amine (1.044 g, 4 mmol), (4-phenoxyphenyl)boronic acid (0.94 g, 4.4 mmol, 1.1 eq), PdCl$_2$(dppf) (0.29 g, 0.4 mmol, 0.1 eq) and Na$_2$CO$_3$ (0.89 g, 8.4 mmol, 2.1 eq) in a 40 ml reaction vial under vacuum, 25 mL of H$_2$O/THF (1:4) is added via a syringe. The mixture is refilled with N$_2$ and heated to 110° C. overnight. TLC showed that the reaction is almost completed. Then solvent is evaporated and the residue is suspended in 200 mL (15% THF/EtOAc) and washed with water, brine, dried over Na$_2$SO$_4$, filtered, and evaporated. The residue is purified with a 50 g silica gel cartridge by Combi-flash (0-10% gradient of methanol in DCM to afford 513 mg of 3-(4-phenoxyphenyl)-1H-pyrazolo[3,4-d]pyrimidin-4-amine.

$^1$HNMR (300 MHz, DMSO-d$_6$): δ 8.22 (s, 1H), 7.66 (d, 2H), 7.43 (t, 2H), 7.10-7.23 (m, 5H).

Step 2: tert-butyl 6-(4-amino-3-(4-phenoxyphenyl)-1H-pyrazolo[3,4-d]pyrimidin-1-yl)-2-azaspiro[3.3]heptane-2-carboxylate

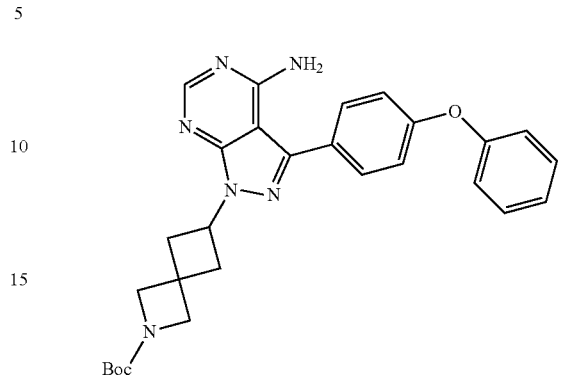

To a mixture of 3-(4-phenoxyphenyl)-1H-pyrazolo[3,4-d]pyrimidin-4-amine (100 mg, 0.33 mmol), tert-butyl 6-hydroxy-2-azaspiro[3.3]heptane-2-carboxylate (141 mg, 0.66 mmol, 2 eq), triphenylphosphine (173 mg, 0.66 mmol, 2 eq) in a 40 ml reaction vial under vacuum, 5 mL of THF is added via a syringe. The mixture is refilled with N$_2$ and DIAD (0.13 mL, 0.66 mmol, 2 eq) is added dropwise at rt. The mixture is then stirred at rt overnight. TLC showed that the reaction is almost completed. Then solvent is evaporated and the residue is purified with a 24 g silica gel cartridge by combi-flash (0-10% gradient of methanol in DCM to afford 78 mg of tert-butyl 6-(4-amino-3-(4-phenoxyphenyl)-1H-pyrazolo[3,4-d]pyrimidin-1-yl)-2-azaspiro[3.3]heptane-2-carboxylate.

$^1$HNMR (300 MHz, acetone-d$_6$): δ 8.26 (s, 1H), 7.78 (d, 2H), 7.46 (t, 2H), 7.10-7.23 (m, 5H), 5.30-5.45 (m, 1H), 4.11 (s, 2H), 4.05 (s, 2H), 2.71-3.0 (m, 4H), 1.44 (s, 9H).

Step 3: 3-(4-phenoxyphenyl)-1-(2-azaspiro[3.3]heptan-6-yl)-1H-pyrazolo[3,4-d]pyrimidin-4-amine

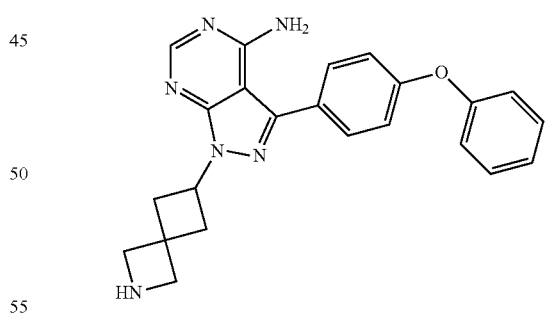

A solution of tert-butyl 6-(4-amino-3-(4-phenoxyphenyl)-1H-pyrazolo[3,4-d]pyrimidin-1-yl)-2-azaspiro[3.3]heptane-2-carboxylate (89 mg, 0.18 mmol in a 3.6 ml of formic acid (85%) is sonicated at rt for 1.5 hr (bath temperature raised to 45-50° C.). The solvent is evaporated and the residue is purified with a 50 g silica gel cartridge by combi-flash (0-100% gradient of Solvent B/DCM, while Solvent B is prepared by mixing 400 mL of DCM with 100 mL of 20% ammonia in methanol) to afford 47 mg of 3-(4-phenoxyphenyl)-1-(2-azaspiro[3.3]heptan-6-yl)-1H-pyrazolo[3,4-d]pyrimidin-4-amine.

¹HNMR (300 MHz, CDC₃): δ 8.33 (s, 1H), 7.67 (d, 2H), 7.39 (t, 2H), 7.05-7.21 (m, 5H), 5.25-5.35 (m, 1H), 3.86 (s, 2H), 3.78 (s, 2H), 2.90-3.02 (m, 2H), 2.68-2.84 (m, 2H).

Step 4: 1-(6-(4-amino-3-(4-phenoxyphenyl)-1H-pyrazolo[3,4-d]pyrimidin-1-yl)-2-azaspiro[3.3]heptan-2-yl)prop-2-en-1-one

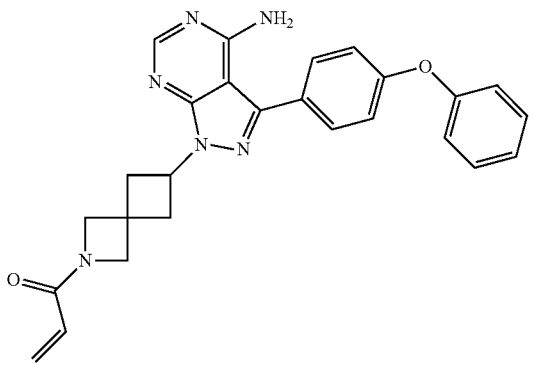 [SMILES: C=CC(=O)N1CC2(CC(n3nc(-c4ccc(Oc5ccccc5)cc4)c4c(N)ncnc43)C2)C1]

To a solution of 3-(4-phenoxyphenyl)-1-(2-azaspiro[3.3]heptan-6-yl)-1H-pyrazolo[3,4-d]pyrimidin-4-amine (48 mg, 0.12 mmol) and 0.05 mL of triethylamine (3 eq) in 2.4 ml of DCM stirred at −78° C. is added acryloyl chloride (1.29 M, 0.093 mL, 0.12 mmol, 1 eq) dropwise. The reaction is warmed up to rt and stirred for 2 hr. The reaction is worked up by the addition of saturated sodium bicarbonate solution. The organic layer is separated and the aqueous phase is extracted with DCM, dried over Na₂SO₄, filtered, and evaporated. The residue is purified with a 24 g silica gel cartridge by Combi-flash (0-100% gradient of Solvent B/DCM, while Solvent B is 10% methanol/acetate) to afford 25 mg of 1-(6-(4-amino-3-(4-phenoxyphenyl)-1H-pyrazolo[3,4-d]pyrimidin-1-yl)-2-azaspiro[3.3]heptan-2-yl)prop-2-en-1-one.

¹HNMR (300 MHz, DMSO-d₆): δ 8.24 (s, 1H), 7.67 (d, 2H), 7.44 (t, 2H), 7.05-7.23 (m, 5H), 6.20-6.40 (m, 1H), 6.09 (d, 1H), 5.41-5.51 (m, 1H), 5.21-5.36 (m, 1H), 4.39 (s, 1H), 4.29 (s, 1H), 4.10 (s, 1H), 4.00 (s, 1H), 2.65-2.95 (m, 4H).

EXAMPLE 2

1-(2-(4-amino-3-(4-phenoxyphenyl)-1H-pyrazolo[3,4-d]pyrimidin-1-yl)-7-azaspiro[3.5]nonan-7-yl)prop-2-en-1-one

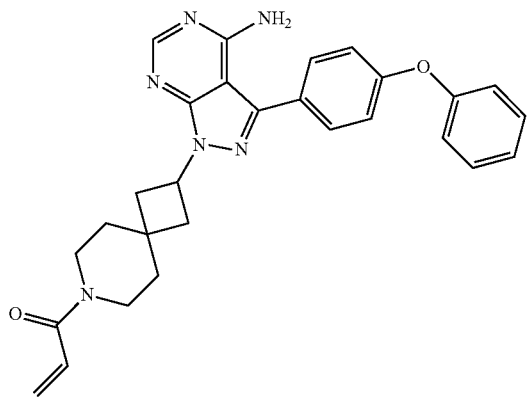 [SMILES: C=CC(=O)N1CCC2(CC1)CC(n1nc(-c3ccc(Oc4ccccc4)cc3)c3c(N)ncnc31)C2]

Step 1: tert-butyl 2-(4-amino-3-(4-phenoxyphenyl)-1H-pyrazolo[3,4-d]pyrimidin-1-yl)-7-azaspiro[3.5]nonane-7-carboxylate

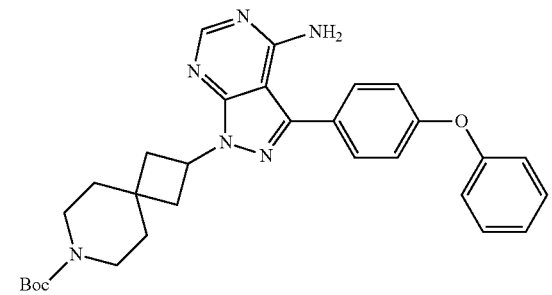 [SMILES: CC(C)(C)OC(=O)N1CCC2(CC1)CC(n1nc(-c3ccc(Oc4ccccc4)cc3)c3c(N)ncnc31)C2]

To a suspension of 3-(4-phenoxyphenyl)-1H-pyrazolo[3,4-d]pyrimidin-4-amine (210 mg, 0.692 mmol, 1.0 equiv), tert-butyl 2-hydroxy-7-azaspiro[3.5]nonane-7-carboxylate (334 mg, 1.385 mmol, 2.0 equiv) and Ph₃P (363 mg, 1.385 mmol, 2.0 equiv) in THF (dry, 5 mL) is added DIAD (0.273 mL, 1.385 mmol, 2.0 equiv) by syringe dropwise at 0° C. under N₂. After addition, the reaction solution is allowed to warm to room temperature slowly and stirred at room temperature overnight. The mixture is concentrated by evaporator in vacuo to give a residue which is purified by CombiFlash [25 g silicagel column, (EtOAc/MeOH=10/1)/Hexane: 0-100%] to give tert-butyl 2-(4-amino-3-(4-phenoxyphenyl)-1H-pyrazolo[3,4-d]pyrimidin-1-yl)-7-azaspiro[3.5]nonane-7-carboxylate, which is submitted for next reaction without further purification.

Step 2: 3-(4-phenoxyphenyl)-1-(7-azaspiro[3.5]nonan-2-yl)-1H-pyrazolo[3,4-d]pyrimidin-4-amine

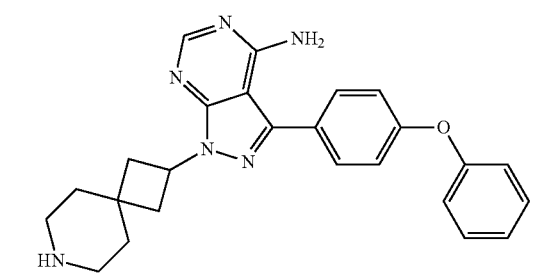 [SMILES: Nc1ncnc2c1c(-c1ccc(Oc3ccccc3)cc1)nn2C1CC2(CCNCC2)C1]

To a solution of tert-butyl 2-(4-amino-3-(4-phenoxyphenyl)-1H-pyrazolo[3,4-d]pyrimidin-1-yl)-7-azaspiro[3.5]nonane-7-carboxylate (360 mg, 0.684 mmol, 1.0 equiv) in DCM (10 mL) is added a solution of HCl in dioxane (4.0 N, 3 mL). The reaction mixture is stirred at room temperature for 1 h. TLC indicated that starting material is consumed. The reaction mixture is concentrated by evaporator in vacuo to give a residue which is purified by CombiFlash [25 g silicagel column, {[(MeOH/NH₄OH=4/1)/DCM]=4/1}/DCM: 0-60%] to give 25 mg (yield 8.6%) of 3-(4-phenoxyphenyl)-1-(7-azaspiro[3.5]nonan-2-yl)-1H-pyrazolo[3,4-d]pyrimidin-4-amine as a white solid.

LC-MS: 427.3 (M$^+$+1, ESI)

Step 3: 1-(2-(4-amino-3-(4-phenoxyphenyl)-1H-pyrazolo[3,4-d]pyrimidin-1-yl)-7-azaspiro[3.5]nonan-7-yl)prop-2-en-1-one Step 1: tert-butyl 7-(4-amino-3-(4-phenoxyphenyl)-1H-pyrazolo[3,4-d]pyrimidin-1-yl)-2-azaspiro[3.5]nonane-2-carboxylate

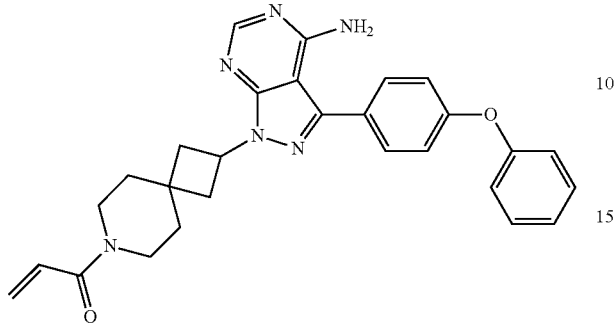

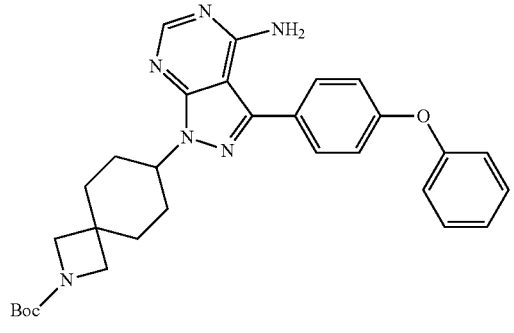

To a solution of 3-(4-phenoxyphenyl)-1-(7-azaspiro[3.5]nonan-2-yl)-1H-pyrazolo[3,4-d]pyrimidin-4-amine (25 mg, 0.059 mmol, 1.0 equiv) and triethylamine (25 μL, 0.176 mmol, 3.0 eqiuv) in DCM (2 mL) is added a solution of acryloyl chloride in DCM (1.29 M, 45 μL, 0.059 mmol, 1.0 equiv) at −78° C. under nitrogen. It is allowed to warm to room temperature slowly and stirred at room temperature overnight. The reaction solution is concentrated by evaporator in vacuo to give a solid which is purified by CombiFlash [12 g silicagel column, [(EtOAc/MeOH=10/1)/Hexane: 0-100%] to give 7.4 mg (26%) of 1-(2-(4-amino-3-(4-phenoxyphenyl)-1H-pyrazolo[3,4-d]pyrimidin-1-yl)-7-azaspiro[3.5]nonan-7-yl)prop-2-en-1-one as a white solid.

$^1$H NMR (acetone-d6, 500 MHz): δ 8.25 (s, 1H), 7.78 (d, 2H), 7.46 (t, 2H), 7.17 (m, 5H), 6.81 (m, 1H), 6.16 (dd, 1H), 5.63 (dd, 1H), 5.49 (m, 1H), 3.66 (m, 2H), 3.56 (m, 2H), 2.61 (m, 2H), 2.50 (m, 2H), 1.78 (m, 4H).

LC-MS: 481.3 (M$^+$+H$^+$, ESI)

To a suspension of 3-(4-phenoxyphenyl)-1H-pyrazolo[3,4-d]pyrimidin-4-amine (135 mg, 0.445 mmol, 1.0 equiv), tert-butyl 7-hydroxy-2-azaspiro[3.5]nonane-2-carboxylate (215 mg, 0.89 mmol, 2.0 equiv) and Ph$_3$P (233 mg, 0.89 mmol, 2.0 equiv) in THF (dry, 5 mL) is added DIAD (175 μL, 0.89 mmol, 2.0 equiv) by syringe dropwise at 0° C. under N$_2$. After addition, the reaction solution is allowed to warm to room temperature slowly and stirred at room temperature overnight. The mixture is concentrated by evaporator in vacuo to give a residue which is purified by CombiFlash [25 g silicagel column, (EtOAc/MeOH=10/1)/Hexane: 0-100%] to give tert-butyl 7-(4-amino-3-(4-phenoxyphenyl)-1H-pyrazolo[3,4-d]pyrimidin-1-yl)-2-azaspiro[3.5]nonane-2-carboxylate, which is used directly for next reaction without further purification.

Step 2: 3-(4-phenoxyphenyl)-1-(2-azaspiro[3.5]nonan-7-yl)-1H-pyrazolo[3,4-d]pyrimidin-4-amine

EXAMPLE 3

1-(7-(4-amino-3-(4-phenoxyphenyl)-1H-pyrazolo[3,4-d]pyrimidin-1-yl)-2-azaspiro[3.5]nonan-2-yl)prop-2-en-1-one

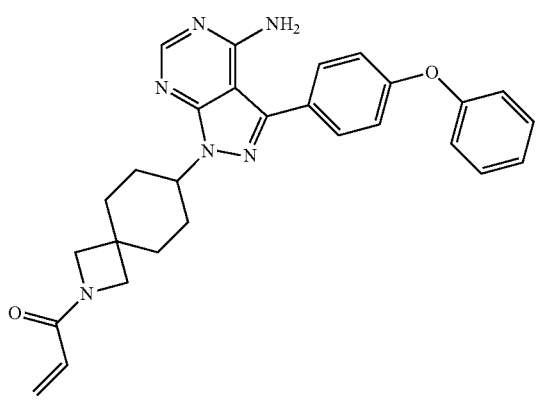 [SMILES: C=CC(=O)N1CC2(CCC(n3nc(-c4ccc(Oc5ccccc5)cc4)c4c(N)ncnc43)CC2)C1]

A solution of tert-butyl 7-(4-amino-3-(4-phenoxyphenyl)-1H-pyrazolo[3,4-d]pyrimidin-1-yl)-2-azaspiro[3.5]nonane-2-carboxylate (230 mg, 0.437 mmol, 1.0 equiv) in formic acid (6 mL) is sonicated for 1.5 hrs. TLC indicated that starting material is consumed. The mixture is concentrated by evaporator in vacuo to give a brown residue which is purified by CombiFlash (25 g silicagel column, {[(MeOH/NH$_4$OH=4/1)/DCM]=4/1}/DCM: 0-60%) to afford 110 mg (59%) of 3-(4-phenoxyphenyl)-1-(2-azaspiro[3.5]nonan-7-yl)-1H-pyrazolo[3,4-d]pyrimidin-4-amine as a pale yellow solid.

LC-MS: 427.3 (M$^+$+H$^+$, ESI)

Step 3: 1-(7-(4-amino-3-(4-phenoxyphenyl)-1H-pyrazolo[3,4-d]pyrimidin-1-yl)-2-azaspiro[3.5]nonan-2-yl)prop-2-en-1-one

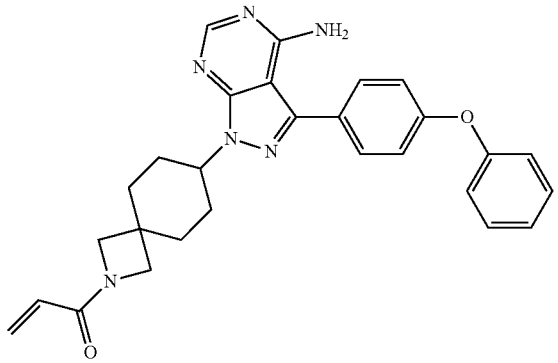 [SMILES: C=CC(=O)N1CC2(CCC(n3nc(-c4ccc(Oc5ccccc5)cc4)c4c(N)ncnc43)CC2)C1]

To a solution of 3-(4-phenoxyphenyl)-1-(2-azaspiro[3.5]nonan-7-yl)-1H-pyrazolo[3,4-d]pyrimidin-4-amine (110 mg, 0.258 mmol, 1.0 equiv) and triethylamine (108 μL, 0.774 mmol, 3.0 equiv) in DCM (5 mL) is added a solution of acryloyl chloride in DCM (1.29 M, 200 μL, 0.258 mmol, 1.0 equiv) at −78° C. under nitrogen. It is allowed to warm to room temperature slowly and stirred at room temperature overnight. It is concentrated by evaporator in vacuo to give a yellow solid which is purified by CombiFlash [25 g silicagel column, [(EtOAc/MeOH=10/1)/Hexane: 0-100%] to give 63 mg (yield 51%) of 1-(7-(4-amino-3-(4-phenoxyphenyl)-1H-pyrazolo[3,4-d]pyrimidin-1-yl)-2-azaspiro[3.5]nonan-2-yl)prop-2-en-1-one as a white solid.

$^1$H NMR (acetone-$d_6$, 400 MHz): δ 8.25 (s, 1H), 7.75 (d, 2H), 7.44 (t, 2H), 7.16 (m, 5H), 6.36 (m, 1H), 6.20 (m, 1H), 5.61 (d, 1H), 4.78 (m, 1H), 4.11 (s, 1H), 3.97 (s, 1H), 3.81 (s, 1H), 3.67 (s, 1H), 1.98 (m, 8H).

LC-MS: 481.3 (M$^+$+H, ESI)

EXAMPLE 4

1-(2-(4-amino-3-(4-phenoxyphenyl)-1H-pyrazolo[3,4-d]pyrimidin-1-yl)-6-azaspiro[3.5]nonan-6-yl)prop-2-en-1-one

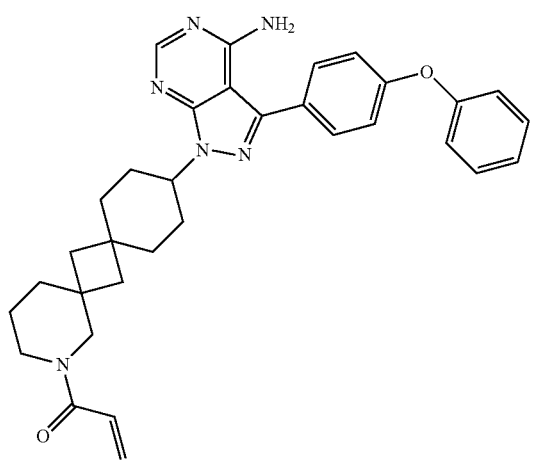 [SMILES: C=CC(=O)N1CCCC2(C1)CC1(CCC(n3nc(-c4ccc(Oc5ccccc5)cc4)c4c(N)ncnc43)CC1)C2]

Step 1: benzyl 2-(4-amino-3-(4-phenoxyphenyl)-1H-pyrazolo[3,4-d]pyrimidin-1-yl)-6-azaspiro[3.5]nonane-6-carboxylate

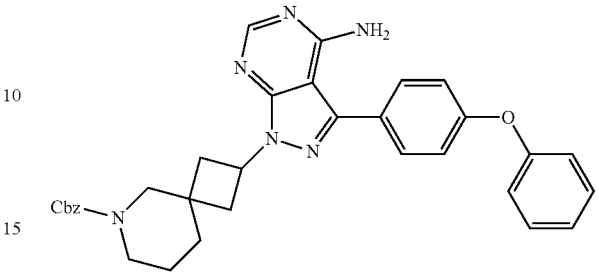

To a suspension of 3-(4-phenoxyphenyl)-1H-pyrazolo[3,4-d]pyrimidin-4-amine (285 mg, 0.94 mmol, 1.0 equiv), benzyl 2-hydroxy-6-azaspiro[3.5]nonane-6-carboxylate (517 mg, 1.88 mmol, 2.0 equiv) and Ph$_3$P (493 mg, 1.88 mmol, 2.0 equiv) in THF (dry, 5 mL) is added DIAD (370 μL, 1.88 mmol, 2.0 equiv) by syringe dropwise at 0° C. under N$_2$. After addition, the reaction solution is allowed to warm to room temperature slowly and stirred at room temperature overnight. The mixture is concentrated by evaporator in vacuo to give the residue which is purified by CombiFlash [25 g silicagel column, (EtOAc/MeOH=10/1)/Hexane: 0-100%] to give crude benzyl 2-(4-amino-3-(4-phenoxyphenyl)-1H-pyrazolo[3,4-d]pyrimidin-1-yl)-6-azaspiro[3.5]nonane-6-carboxylate, which is employed directly for next reaction without further purification.

Step 2: 3-(4-phenoxyphenyl)-1-(6-azaspiro[3.5]nonan-2-yl)-1H-pyrazolo[3,4-d]pyrimidin-4-amine

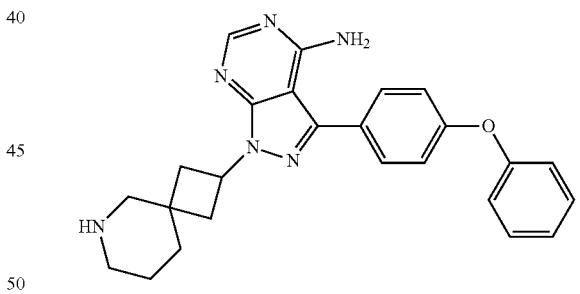

To a solution of crude benzyl 2-(4-amino-3-(4-phenoxyphenyl)-1H-pyrazolo[3,4-d]pyrimidin-1-yl)-6-azaspiro[3.5]nonane-6-carboxylate (530 mg, 0.945 mmol, 1.0 equiv) in THF/MeOH (5/5 mL) is added with Pd(OH)$_2$ (80 mg, 20 wt % (dry basis) on carbon) in one portion. The mixture is stirred at room temperature under H$_2$ balloon for 18 hrs. Pd(OH)$_2$ (60 mg) and acetic acid (4 mL) are added. The mixture is stirred at room temperature under H$_2$ balloon for 30 hrs. The mixture is passed through a pad of celite, eluted with MeOH (30 mL). The combined filtrate is concentrated by evaporator in vacuo to give a residue which is purified by CombiFlash (25 g silicagel column, {[(MeOH/NH$_4$OH=4/1)/DCM]=4/1}/DCM: 0-60%) to afford 77 mg (59%) of 3-(4-phenoxyphenyl)-1-(6-azaspiro[3.5]nonan-2-yl)-1H-pyrazolo[3,4-d]pyrimidin-4-amine as a pale yellow solid.

LC-MS: 427.3 (M$^+$+H$^+$, ESI)

Step 3: 1-(2-(4-amino-3-(4-phenoxyphenyl)-1H-pyrazolo[3,4-d]pyrimidin-1-yl)-6-azaspiro[3.5]nonan-6-yl)prop-2-en-1-one

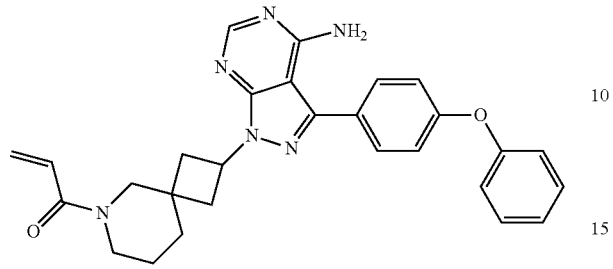

To a solution of 3-(4-phenoxyphenyl)-1-(6-azaspiro[3.5]nonan-2-yl)-1H-pyrazolo[3,4-d]pyrimidin-4-amine (77 mg, 0.181 mmol, 1.0 equiv) and triethylamine (108 μL, 0.774 mmol, 3.0 equiv) in DMF/DCM (dry, 3/1 mL) is added a solution of acryloyl chloride in DCM (1.29 M, 200 μL, 0.258 mmol, 1.4 equiv) at −78° C. under nitrogen. After addition, the solution is allowed to warm to room temperature slowly, and then stirred at room temperature overnight. It is concentrated by evaporator in vacuo to give a yellow solid which is purified by CombiFlash [10 g silicagel column, [(EtOAc/MeOH=10/1)/Hexane: 0-100%] to give 18 mg of Example 4A, a pure diasteromer (cis or trans unidentified) of 1-(7-(4-amino-3-(4-phenoxyphenyl)-1H-pyrazolo[3,4-d]pyrimidin-1-yl)-2-azaspiro[3.5]nonan-2-yl)prop-2-en-1-one as a white solid [LC-MS: 481.3 (M$^+$+H, ESI)], followed by 2.4 mg of Example 4B, a mixture of diasteromers (cis/trans≈1/1) of 1-(7-(4-amino-3-(4-phenoxyphenyl)-1H-pyrazolo[3,4-d]pyrimidin-1-yl)-2-azaspiro[3.5]nonan-2-yl)prop-2-en-1-one as a white solid. LC-MS: 481.3 (M$^+$+H, ESI).

BIOCHEMICAL EVALUATION

The BTK inhibitory activities of compounds of Formula A are assayed at Reaction Biology Corporation, One Great Valley Parkway, Malvern, Pa., USA. Human BTK enzyme is used and the substrate is a peptide substrate, [KVEKIGEGTYGVVYK] at 20 μM. The ATP concentration for the assay is 10 μM and Staurosporine is used as a standard with an IC$_{50}$ of 3.94 nM.

TABLE 3

Inhibitory Activities of examples at 5 nM

| Compound | Inhibition of ALK, IC$_{50}$ |
| --- | --- |
| EXAMPLE 1 | 98.5% |
| EXAMPLE 2 | 80.1% |
| EXAMPLE 3 | 96.4% |
| EXAMPLE 4A | 85.7% |
| EXAMPLE 4B | 97.9% |

The IC$_{50}$ of Example 1 is measured to be 1.48 nM.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A compound of Formula (B)

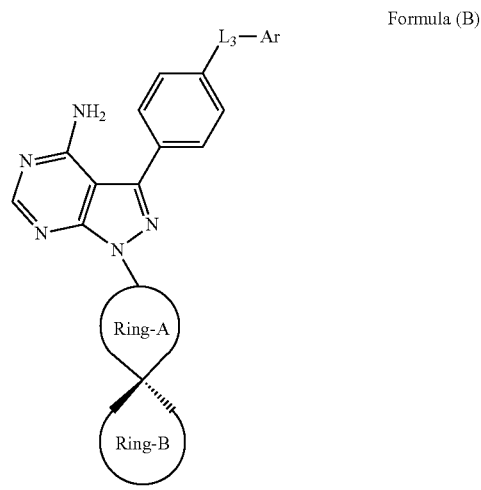

Formula (B)

or a pharmaceutically acceptable salt, hydrate or solvate thereof, wherein:

is selected from the group consisting of:

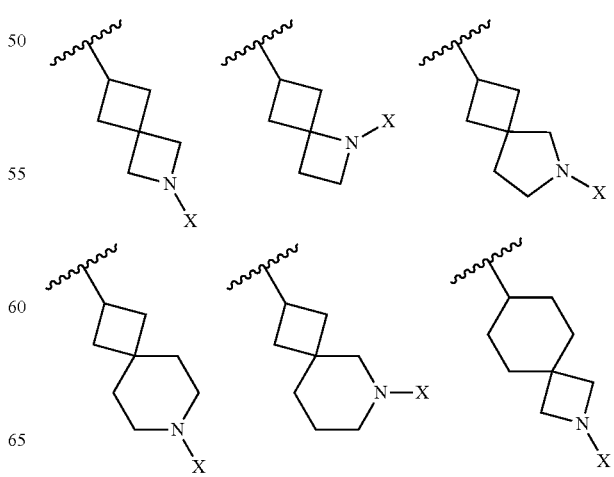

-continued

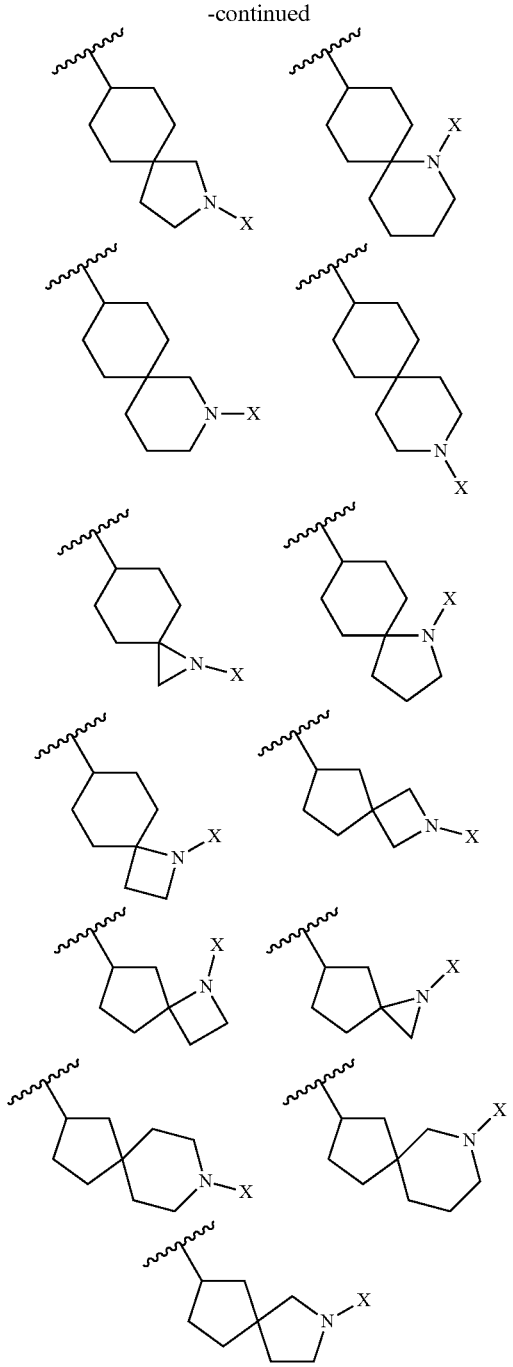

X is:

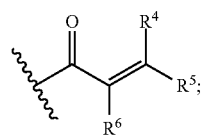

$R^5$, $R^4$ and $R^6$ are independently selected from H, $C_{1-12}$alkyl, $C_{1-12}$heteroalkyl, $C_{1-12}$ heterocycloalkyl, $C_{2-12}$ alkenyl, $C_{2-12}$ alkynyl, $C_{3-12}$ cycloalkyl;

$L_3$ is $CH_2$, O, S, or $NR^d$;

$R^d$ is H, $C_{1-6}$alkyl, $C_{3-6}$cycloalkyl, aryl or heteroaryl;

Ar is an aryl or heteroaryl which is unsubstituted or substituted with one or more $R^e$;

$R^e$ is independently chosen from halogen, $C_{1-12}$alkyl, $C_{2-12}$alkenyl, $C_{2-12}$alkynyl, $C_{3-12}$ cycloalkyl, $C_{6-12}$aryl, a 3-12 membered heteroalicyclic ring, a 5-12 membered heteroaryl ring, —$S(O)_mR^d$, —$S(O)_2NR^dR^d$, —$S(O)_2OR^d$, $SF_5$, —CN, —$NO_2$, —$NR^dR^d$, —C(O)$R^d$, —OC(O)$R^d$, —O(CR$^dR^d)_nR^d$, —$NR^dC(O)R^d$, —(CR$^dR^d)_nC(O)OR^4$, —(CR$^dR^d)_nOR^4$, —(CR$^dR^d)_nC(O)NR^dR^d$, —(CR$^dR^d)_nNCR^dR^d$, —C(=$NR^d$)$NR^dR^d$, —$NR^dC(O)NR^dR^d$, —$NR^dS(O)_2R^d$ or —C(O)$NR^dR^d$, wherein each hydrogen in $R^d$ is unsubstituted or substituted by $R^f$;

wherein two $R^d$ on the same atom are unconnected or connected to form a carbocyclic ring, or two $R^d$ on the same atom are unconnected or connected to form a carbocyclic ring in which one or more carbon ring atoms are replaced with one or more O, S, S(O), $S(O)_2$, C(O), C(S) and $NR^d$;

n is selected from 1 to 6;

$R^f$ is independently chosen from halogen, $C_{1-12}$alkyl, $C_{2-12}$alkenyl, $C_{2-12}$alkynyl, $C_{3-12}$cycloalkyl, $C_{6-12}$aryl, a 3-12 membered heteroalicyclic ring, a 5-12 membered heteroaryl ring, —$NH_2$, —CN, —OH, —O—$C_{1-12}$alkyl, —O—$(CH_2)_nC_{3-12}$cycloalkyl, —O—$(CH_2)_n$ $C_{6-12}$aryl, —O—$(CH_2)_n$ (3-12 membered heteroalicyclic ring) or —O—$(CH_2)_n$ (5-12 membered heteroaryl ring); and two $R^e$ on adjacent atoms are unconnected or connected to form a $C_{6-12}$ aryl ring, a 5-12 membered heteroaryl ring, a $C_{5-20}$ cycloalkyl ring or a 5-20 membered heteroalicyclic ring, or two $R^e$ on adjacent atoms are unconnected or connected or combined to form a $C_{6-12}$ aryl ring, a 5-12 membered heteroaryl ring, a $C_{5-20}$ cycloalkyl ring or a 5-20 membered heteroalicyclic ring which contains one or more heteroatom selected from O, $NR^d$, S.

2. The compound of claim 1, wherein the compound is:
1-(6-(4-Amino-3-(4-phenoxyphenyl)-1H-pyrazolo[3,4-d]pyrimidin-1-yl)-2-azaspiro[3.3]heptan-2-yl)prop-2-en-1-one;

1-(2-(4-amino-3-(4-phenoxyphenyl)-1H-pyrazolo[3,4-d]pyrimidin-1-yl)-7-azaspiro[3.5]nonan-7-yl)prop-2-en-1-one;

1-(7-(4-amino-3-(4-phenoxyphenyl)-1H-pyrazolo[3,4-d]pyrimidin-1-yl)-2-azaspiro[3.5]nonan-2-yl)prop-2-en-1-one; or 1-(2-(4-amino-3-(4-phenoxyphenyl)-1H-pyrazolo[3,4-d]pyrimidin-1-yl)-6-azaspiro[3.5]nonan-6-yl)prop-2-en-1-one.

3. A pharmaceutical composition comprising a compound of claim 1 and a pharmaceutically acceptable carrier.

4. A pharmaceutical composition comprising a compound of claim 1 in combination with an anti-cancer agent selected from cytotoxic agents, antimitotic agents, anti-metabolites, proteasome inhibitors, HDAC inhibitors, a kinase inhibitor, or combination thereof.

5. A method of treating rheumatoid arthritis comprising administering a therapeutically effective amount of a compound of claim 1 to an individual in need thereof.

6. A method of treating rheumatoid arthritis comprising administering a therapeutically effective amount of a compound of claim 1 together with radiotherapy to an individual in need thereof.

* * * * *